United States Patent
Ciarniello et al.

(10) Patent No.: US 6,802,810 B2
(45) Date of Patent: Oct. 12, 2004

(54) CARE ENGINE

(75) Inventors: Anthony Ciarniello, Bethpage, NY (US); Lonny Reisman, Jericho, NY (US); Charles Blanksteen, New York, NY (US)

(73) Assignee: Active Health Management, New York, NY (US)

( * ) Notice: Subject to any disclaimer, the term of this patent is extended or adjusted under 35 U.S.C. 154(b) by 0 days.

(21) Appl. No.: 09/957,473

(22) Filed: Sep. 21, 2001

(65) Prior Publication Data

US 2003/0060688 A1 Mar. 27, 2003

(51) Int. Cl.[7] .......................... A61B 5/00; G06F 17/60
(52) U.S. Cl. .................................. 600/300; 705/2
(58) Field of Search ..................... 600/300, 301; 705/2, 3; 128/920, 923, 924, 925; 706/15, 20, 45, 924

(56) References Cited

U.S. PATENT DOCUMENTS

| | | | | |
|---|---|---|---|---|
| 5,687,716 A | * | 11/1997 | Kaufmann et al. | 600/300 |
| 5,908,383 A | * | 6/1999 | Brynjestad | 600/300 |
| 5,935,060 A | * | 8/1999 | Iliff | 600/300 |
| 5,956,689 A | * | 9/1999 | Everhart, III | 705/3 |
| 5,991,731 A | * | 11/1999 | Colon et al. | 705/3 |
| 6,014,631 A | * | 1/2000 | Teagarden et al. | 705/3 |
| 6,139,494 A | * | 10/2000 | Cairnes | 600/300 |
| 6,223,164 B1 | * | 4/2001 | Seare et al. | 705/2 |
| 6,277,071 B1 | * | 8/2001 | Hennessy et al. | 600/300 |
| 6,551,243 B2 | * | 4/2003 | Bocionek et al. | 600/300 |

\* cited by examiner

*Primary Examiner*—Mary Beth Jones
*Assistant Examiner*—David J. McCrosky
(74) *Attorney, Agent, or Firm*—Greenberg Traurig, LLP

(57) ABSTRACT

The present invention offers a comprehensive solution to care management which aggregates, integrates and stores clinical information from disparate sources. The system finds at-risk individuals before they experience preventable, high-cost medical events and stratifies high risk populations according to clinical criteria, which can include severity of disease states and co-morbidities. The system also compares the actual care an individual is receiving to established standards of clinical excellence and, if necessary, suggests pertinent medical care considerations to improve the care of medically mismanaged individuals. Another feature of the present invention may include a secure, patient-specific Web page which is automatically populated with a patient's own clinical information and can be personalized with customized, relevant healthcare information. The system allows users to design, facilitate and monitor clinical care plans and increase communications among physicians, nurses and patients. The system also predicts and analyzes the outcome of disease or case management for populations and individual patients.

21 Claims, 21 Drawing Sheets

Criteria

Element: Diuretics [Details...]

1611 — Min
1613 — Max
1615 — Date

- Above
- Below
- Greater Than
- Less Than
- Not Observed

FIG. 16

CARE ENGINE

REFERENCE TO RELATED APPLICATIONS

1. Field of the Invention

The present invention relates to a system and methods for medical analysis and more particularly, it relates to an early warning trigger analysis system used as an automated mechanism for the early warning detection of patient health risk.

2. Background of the Invention

The concerns about medical errors and clinical quality are increasing. In fact, a 1999 study by the Institute of Medicine of the National Academy of Sciences estimates that 1.5% to 2.0% of all hospital admissions in the United States result in a significant and preventable adverse event that was caused by the medical establishment. The study estimates that medical mistakes are the eighth leading cause of death in the United States. The delivery of clinical care often involves complex analysis and the evaluation of multiple treatment options. However, many physicians report that, due to the rapid pace of medical innovation and the volume and complexity of medical information directed at them, they have difficulty keeping up with state of the art medical practices and other developments in their areas of specialization.

The public and the media have also become increasingly concerned with healthcare quality. For example, it has been reported that as few as 5% of people in the United States with heart failure receive the appropriate therapy. Further, it is estimated that this failure to apply an optimal therapy results in an estimated 100,000 premature deaths from this condition that otherwise might not have occurred.

Another problem with the health care system is that incomplete patient clinical data leads to inefficiencies and lapses in patient care. All participants in the healthcare system rely heavily on information and often depend on other participants for the information they need to perform their roles. However, individual care is delivered and paid for in numerous locations by individuals and organizations that are often unrelated. As a result, critical patient data is stored in many different locations using incompatible and proprietary legacy mainframe and client-server systems that store information often in non-standardized formats. To diagnose and treat a patient properly, providers must often request patient information by phone or fax from hospitals, laboratories or other providers. The delivery of this information is often delayed and may be incomplete due to the disparate systems maintained by those constituents.

This industry fragmentation and the resulting lack of comprehensive patient information are primary reasons for inefficiencies and lapses in patient care. These inefficiencies and lapses may lead to medical mistakes, poor clinical outcomes and excess costs due to: inconsistent, incomplete or inaccurate diagnoses; redundant tests; inappropriate medications; increased potential for medical errors and clinical complications; and failure to apply optimal therapies and adequate follow-up.

Healthcare expenditures continue to rise and it is estimated that healthcare expenditures currently represent $1.2 trillion, or 14%, of the U.S. economy, and that these expenditures will continue to increase to $2.2 trillion in 2008, an 8% compound annual growth rate, both because of rising healthcare costs and the increasing medical demands of an aging population.

Further, it is also estimated that over $250 billion dollars are wasted each year through the delivery of unnecessary care, performance of redundant tests or procedures and excessive administrative costs. As a result, the government and other purchasers of healthcare have increasingly placed pressure on the industry to improve the quality and cost-effectiveness of healthcare. To date, health plans have primarily focused on gaining price concessions from providers and suppliers and limiting access to healthcare products and services. Recently, consumers, providers and policymakers have begun to question this managed care approach. Patients and their employers have expressed dissatisfaction with escalating health plan premiums and "gatekeeper" style plans that limit physician choice and access to healthcare services. Physicians and patients have expressed concern that managed care has led to a decline in the quality of patient care.

Another problem is that current healthcare information technology approaches do not address the majority of healthcare costs. Information technology and the Internet have become increasingly important tools to manage rising costs in the healthcare industry. However, current healthcare information technology products and services, including many e-health initiatives, focus primarily on changing administrative and financial processes, such as streamlining billing and purchasing, or maximizing reimbursement. Very few of these initiatives address unnecessary or inappropriate clinical care or the overall quality of clinical care. In addition, these administrative-oriented efforts address only the 15% of healthcare expenditures that relate to administrative costs and do not address the 85% of expenditures that relate to clinical costs.

In addition all participants in the healthcare system rely heavily on information and often depend on other participants for the information they need to perform their roles. However, individual care is delivered and paid for in numerous locations by individuals and organizations that are often unrelated. As a result, critical patient data is stored in many different locations using incompatible and proprietary legacy mainframe and client-server systems that store information often in non-standardized formats. To diagnose and treat a patient properly, providers must often request patient information by phone or fax from hospitals, laboratories or other providers. The delivery of this information is often delayed and may be incomplete due to the disparate systems maintained by those constituents.

Therefore what is needed is a healthcare management system which improves the quality of care, better manages healthcare costs, provides healthcare organizations and physicians information to make accurate diagnosis and treatment, and provides a communications link for information, forms, patients, healthcare organizations and physicians.

SUMMARY OF THE INVENTION

The present invention counters the problems associated with healthcare management by providing a clinically sophisticated, comprehensive solution to improve the quality and manage the costs of care. The present invention includes software applications and services that are broadly organized under three product/service offerings including: (i) application tools for identifying potentially problematic patient cases before they become effective problems, (ii) case and disease management applications and programs for managing problematic and complex cases and (iii) applications and services to improve overall risk underwriting profitability.

The foundations of the present invention are its unique data repository and its proprietary Care Engine™, multi-dimensional analytical software tool. The Care Engine software tool is developed around broad categories of diseases and treatments, with defined elements called matrices. The present invention has been developed together with a panel of board-certified medical specialists and encompasses an array of care management functions, including: (1) screening patient populations; (2) finding and stratifying high-risk patients within a population; (3) identifying potential misdiagnoses or errors in care; (4) providing information that enables physicians to improve the care of poorly managed or misdiagnosed patients; (5) creating software tools for the case management of patients with complex, acute or chronic diseases; and (6) providing predictive tools to improve the accuracy of healthcare risk underwriting.

The present invention may be provided through an application service provider model either as a complete care management solution or separately, depending on the customer's needs. The present invention users will include self-insured employers, payers, and TPAs.

The present invention securely aggregates and standardizes clinical data derived from a variety of sources and stores it on a patient-specific basis in a unique data repository, called the DataVault. As seen in FIG. 1 these data types include laboratory test results 103, prescription drug data 101, health plan claims data 105, and in-patient information and notes 107. The laboratory test results 103, prescription drug data 101, health plan claims data 105, and in-patient information and notes 107 can be sent to an analytical portion of the system through a data link 109. Once the various different kinds of data are sent they are stored in a Data Vault 110. The analytical portion of the present invention is the Care Engine 112 which is used to analyze a patient's available medical history. The Care Engine 112 identifies potential diagnostic or treatment errors to enable timely modification to treatment regimens. The Care Engine 112 can also find individuals and stratify populations by numerous-adjusted disease criteria and co-morbidities, allowing customers to assess the need for and implement appropriate disease or case management programs. The present invention also uses a screening element 115 which allows medical staff to review or screen potential diagnostic or treatment errors discovered by the Care Engine 112.

In addition, the present invention may incorporate secure, individual patient Web pages, which it calls Private Health Records 130, that are designed to educate and empower individuals to participate in healthcare decisions and may include customers, physicians, and patients. The Private Health Records 130 would be available through a system portal 120 and web browser 125. The Care Engine 112 will automatically populate a patient's Private Health Record 130 with information stored in the DataVault 110. However, the screening element 115 will filter out information corresponding with the type of user such that only that information for which they are provided access to can be viewed.

Another failure of the system of the present invention includes a rules-driven, Internet-based, easily customizable process, or workflow, software platform that is delivered over the Internet. Customers may use this platform to create and develop nurse-supported case management and disease management programs for patients with complex, acute or chronic diseases.

The system is also designed to predict medical care costs within a covered population by using epidemiological and demographic data, as well as the clinical data aggregation and analysis capabilities provided by the DataVault 110 and Care Engine 112. Customers would use these products and services to assess the potential cost savings of different disease management strategies and clinical interventions, and identify the members of a covered population who are being medically mismanaged and whose associated medical costs could be affected by timely treatment intervention.

The present invention offers a comprehensive solution to care management which: aggregates, integrates and stores clinical information from disparate sources; finds at-risk individuals for case management before they experience preventable, high-cost medical events; stratifies high risk populations according to clinical criteria, which can include severity of disease states and co-morbidities; compares the actual care an individual is receiving to established standards of clinical excellence and, if necessary, suggests pertinent medical care considerations to improve the care of medically mismanaged individuals; creates a secure, patient-specific Web page that is automatically populated with a patient's own clinical information and further personalizes with customized, relevant healthcare information; allows users to design, facilitate and monitor clinical care plans and increase communications among physicians, nurses and patients; and predicts and analyzes the outcome of disease or case management for populations and individual patients.

BRIEF DESCRIPTION OF THE DRAWINGS

FIG. 10 is an illustrative example of a user interface in a preferred embodiment of the present invention displaying the Matrix Element Maintenance screen with matching NDC codes.

Figure 11:
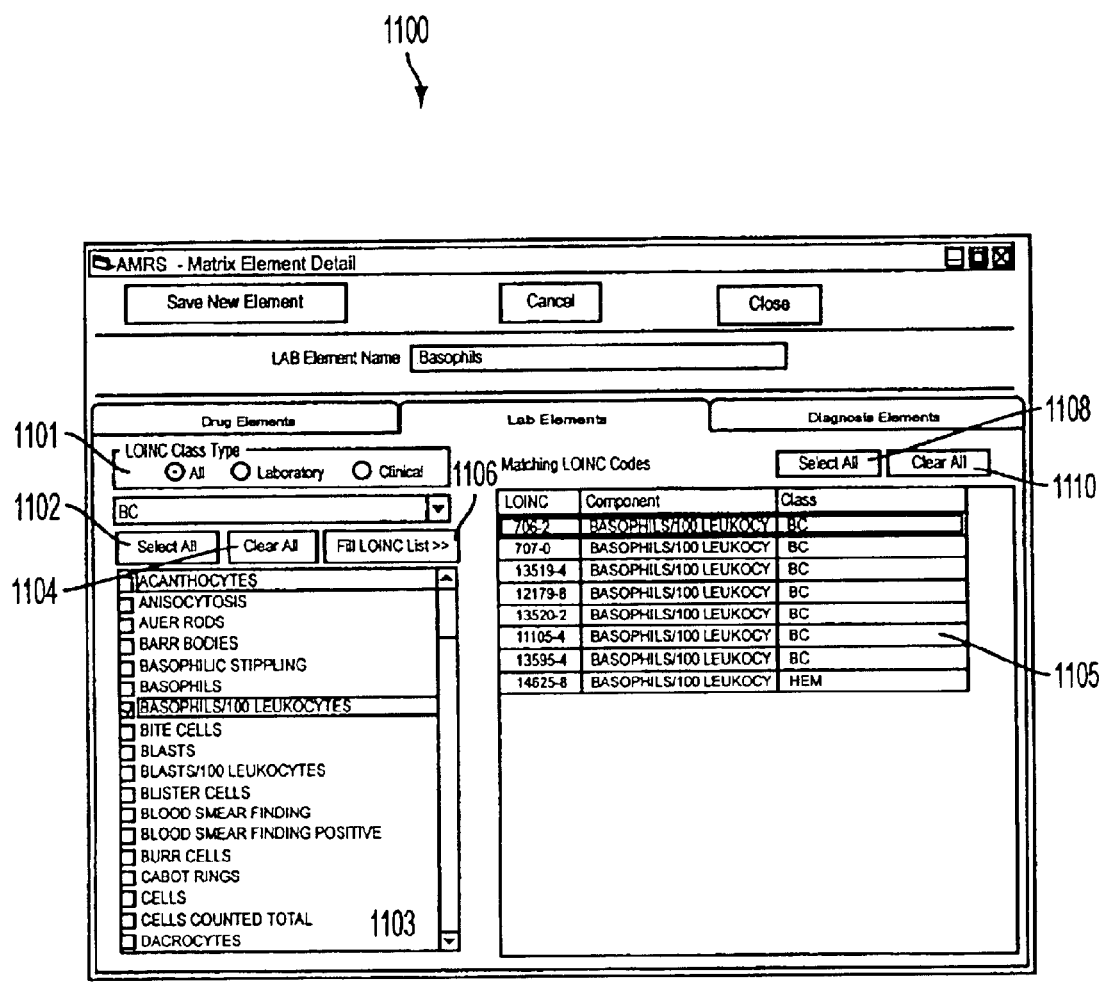

FIG. 11 is an illustrative example of a user interface in a preferred embodiment of the present invention displaying the Matrix Element Maintenance screen with matching LOINC codes.

FIG. 16 is an illustrative example of a user interface in a preferred embodiment of the present invention displaying the range criteria drop down list.

DETAILED DESCRIPTION OF THE PREFERRED EMBODIMENT

Figure 2:
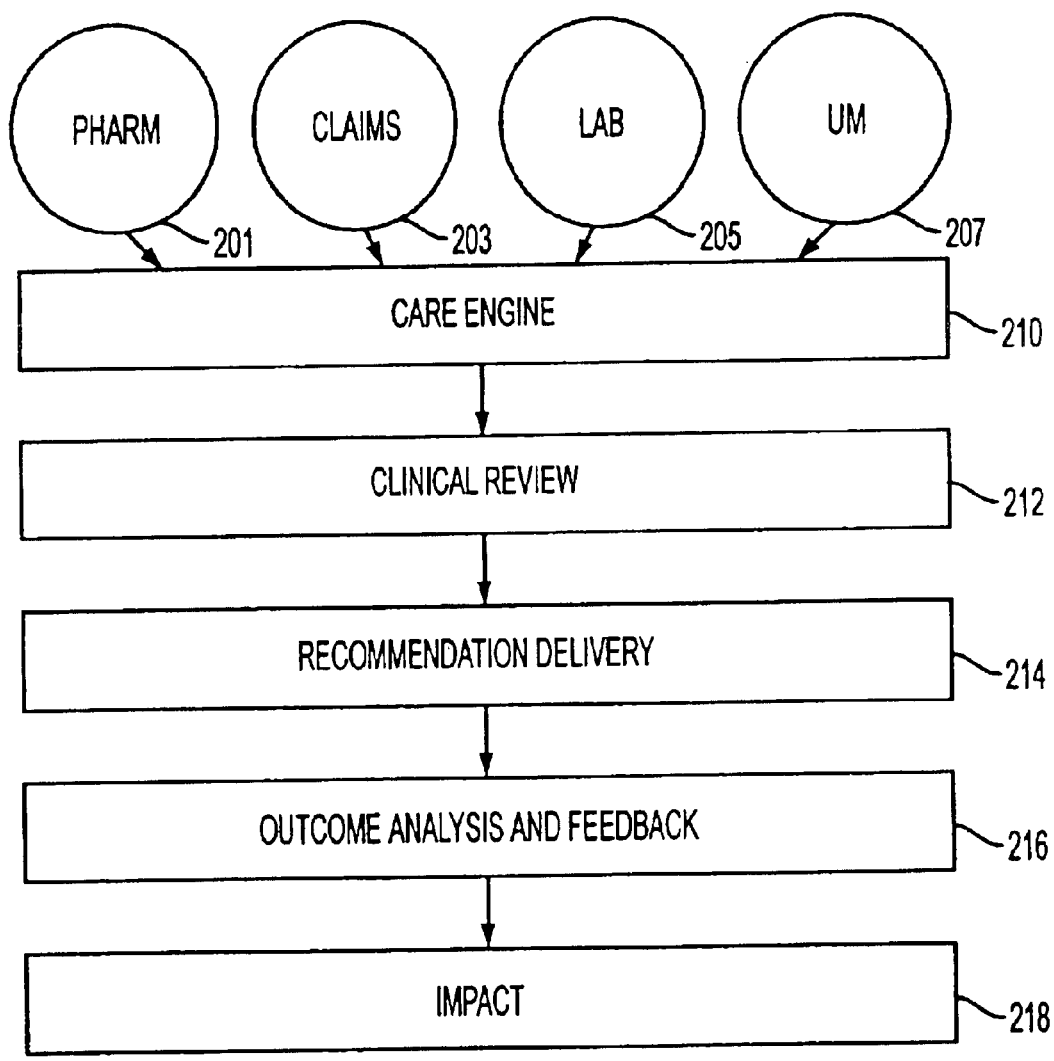
FIG. 2 is a schematic illustration of data flow through the system of the present invention.

The present invention offers a unique solution to many of these industry issues. By combining proprietary technology with the benefits of the Internet, the present invention provides a complete clinical care management solution. The complete solution will be described in conjunction with FIG. 2.

The present invention is able to identify sub-optimal care and potential clinical errors. The Care Engine's software tool 210 uses proprietary clinical matrices to comb through high volumes of patient data to identify potential diagnostic or treatment errors. The present invention integrates clinical information, such as laboratory test results 205, prescription drug data 201, health plan claims data 203 and in-patient claims data and notes 207 to create a comprehensive picture of a patient's health and treatment status, analyzes this information using the matrices embedded in the Care Engine 210 and identifies potential deficiencies in a patient's medical care.

The present invention also assists in determining Optimal Treatment Strategies. When the Care Engine 211 identifies a potential deficiency in the medical care being provided to a patient, the present invention provides the available information to medical staff for clinical review 212. The present invention then provides the pertinent medical care considerations or treatment alternatives to its customers and provides medical literature to support the care considerations to a recommendation delivery 214. This information is typically provided by the customer, such as a health care organization, to the treating physician to effect changes in a patient's clinical management. The present invention also keeps track of the treatment and provides an outcome analysis and feedback step 216 and mines data to determine the impact 218.

The present invention also aggregates and standardizes patient clinical information in a single database. The present invention collects clinical data from a variety of sources, standardizes this data in a single database and aggregates patient-specific medical information in its DataVault. Unlike other healthcare data warehouses or legacy systems that are organized according to types of data, such as lab or insurance claims records, the DataVault of the present invention is architected around individual patients and encompasses all available information about those patients.

The present invention also provides tools to manage patient health, which enables its customers to select appropriate candidates for disease and case management. The present invention's customizable, Internet-based CareSystem workflow software platform assists payers and other at-risk healthcare participants in providing personalized, nurse-supported care management to patients with complex, acute or chronic diseases. Using the present invention's workflow platform, customers will be able to assess a patient's medical and functional status and needs using sophisticated conditional logic tools, identify and prioritize care plan tasks based on that assessment and facilitate and monitor clinical interventions and communications among physicians, nurses and patients.

In addition, the present invention capitalizes on the benefits of the Internet, which includes an open architecture, platform and location independence, scalability and increasing acceptance make it an important and low-cost medium for the information-intensive healthcare industry and make it possible to deliver the applications and services wherever they are needed. The Internet-based approach to clinical care management facilitates efficient, low-cost sharing of information across multiple healthcare constituents in multiple locations. In addition, the Internet enables users to cost-effectively implement a wider spectrum of patient management programs for which it can develop the tools.

Figure 3:
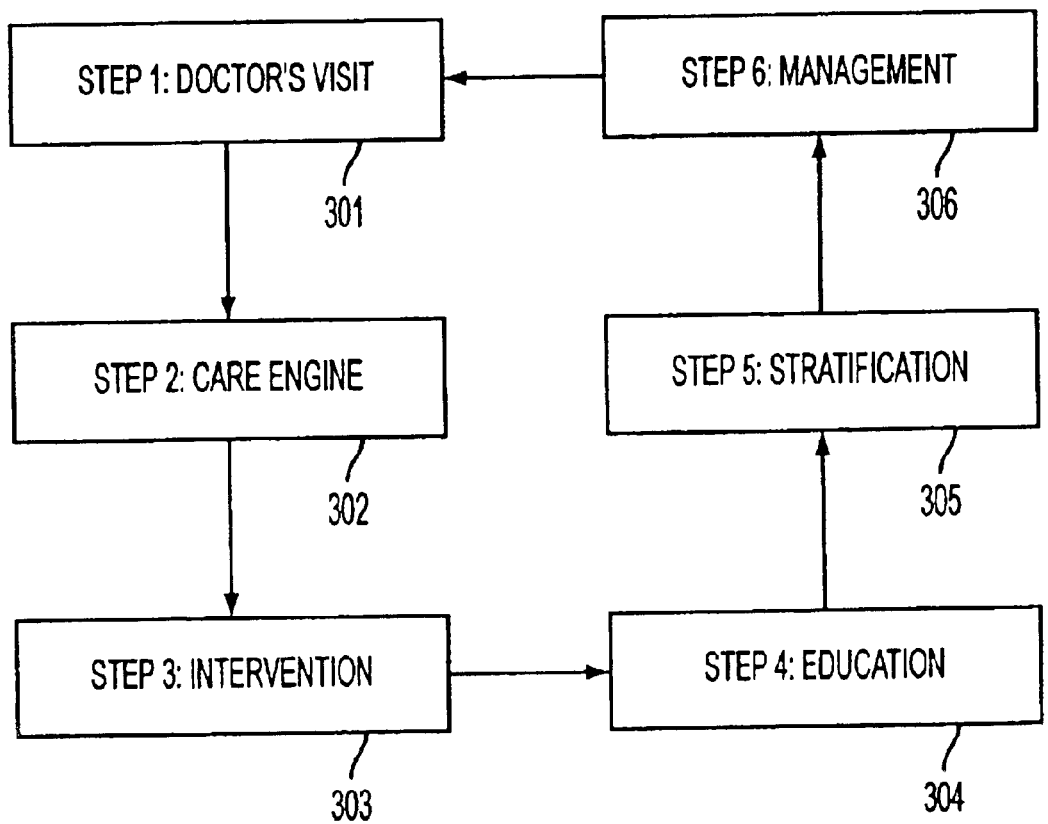
FIG. 3 is a step function diagram of the systems interaction, flow, and use during patient treatment.

FIG. 3 illustrates the applicability of several of the present invention's principal applications and services to the clinical care of a hypothetical patient.

The hypothetical patient, Jane for this example, visits a doctor in step 301. Jane, whose health plan utilizes the present invention, visits an endocrinologist for treatment of diabetes. The DataVault has clinical claims history on Jane showing diabetes and chronic kidney failure. Jane's endocrinologist prescribes metformin hydrochloride tablets (known as Glucophage) for her diabetes. Jane's new prescription and information are input and uploaded to the system.

In step 302, the present invention, through the Care Engine, analyzes available lab, prescription and claims data and finds that Glucophage is not recommended for patients with kidney disease since the combination can lead to a life-threatening condition known as lactic acidosis. The present invention alerts the medical personnel, who review Jane's medical data and confirm that a call to the treating physician is appropriate.

In step 303, medical personnel discuss Jane's case by phone with a member of the health plan's medical staff and provide the health plan with an article from the New England Journal of Medicine that discusses the effects of Glucophage on patients with kidney problems. The health plan's medical staff discuss Jane's case by phone with her treating physician who agrees to stop Jane's treatment with Glucophage immediately and initiate therapy with an alternative, safer drug.

Jane educates herself, at step 304, on alternative blood sugar control methods by reading the personalized medical information on diabetes and kidney failure that she found by logging on to her Private Health Record.

Jane's health plan uses the present invention's Case Finder and Risk Stratifier services to find and stratify its diabetic members by disease severity and co-morbidities. Based on this analysis, Jane's health plan determines that Jane is an appropriate candidate for diabetic disease management in step 305.

Lastly, in step 306, to manage Jane's diabetes, the health plan enrolls Jane in a diabetes management program that uses the present invention's CareSystem, a disease management platform that Jane's health plan customized with its diabetes protocols. Using CareSystem, the health plan's medical staff assess Jane's medical and functional condition and assign Jane and in-house medical staff appropriate compliance and monitoring tasks.

Another feature and tool of the present invention is Care Manager, which is a tool that identifies care intervention opportunities to avoid preventable, dangerous and costly medical events that occur when a patient's medical management differs from recommended standards of treatment. The Care Manager identifies cases that may present care intervention opportunities by running patient data from the DataVault through the proprietary clinical matrices of the Care Engine. The Care Manager obtains patient data through magnetic tapes or electronic data transfers from disparate sources, such as the patient's health plan and laboratories and pharmacy benefit managers. Alternatively, if customers or other entities providing data prefer, the Care Manager is able to receive clinical data over the Internet. The present invention's systems then standardize and sort this data for recognition by software triggers using sophisticated data cleansing techniques.

The Care Engine identifies misdiagnoses, surgical options, lack of follow-up or preventative treatment and drug-to-drug, drug-to-disease and drug-to-metabolic interactions. The Care Engine also uncovers potential conditions that have not been treated, including complications presented when a patient has more than one disease state. The Care Engine covers a broad spectrum of commonly observed disease states and co-morbidities.

Depending upon the nature and complexity of the potential medical complication identified by the Care Engine tool, the systems can refer the case for in-house medical review. Based on the results of this review, if appropriate, advice is given to the patient's health plan of pertinent medical considerations supported by established medical literature that should be considered by the patient's caregiver. The health plan may then decide to contact the patient's physician. These communications can take place by phone, through the Internet, or any other communications link, directly with providers at the point of care. In addition, the present invention incorporates artificial intelligence technology which allows the Care Manager to, in some cases, automatically make a variety of treatment suggestions directly to the health care provider without the need for review by in-house medical staff.

The Care Manager is not designed to deny access to specialist care, but rather guides doctors and patients to the most clinically valid care plan by accelerating patients' access to specialist care or consultation where necessary. Care Manager represents a benefit to customers attempting to design the types of "open access" managed care plans that many healthcare consumers have indicated they prefer, without sacrificing the care coordination provided by primary care physicians.

Figure 1:
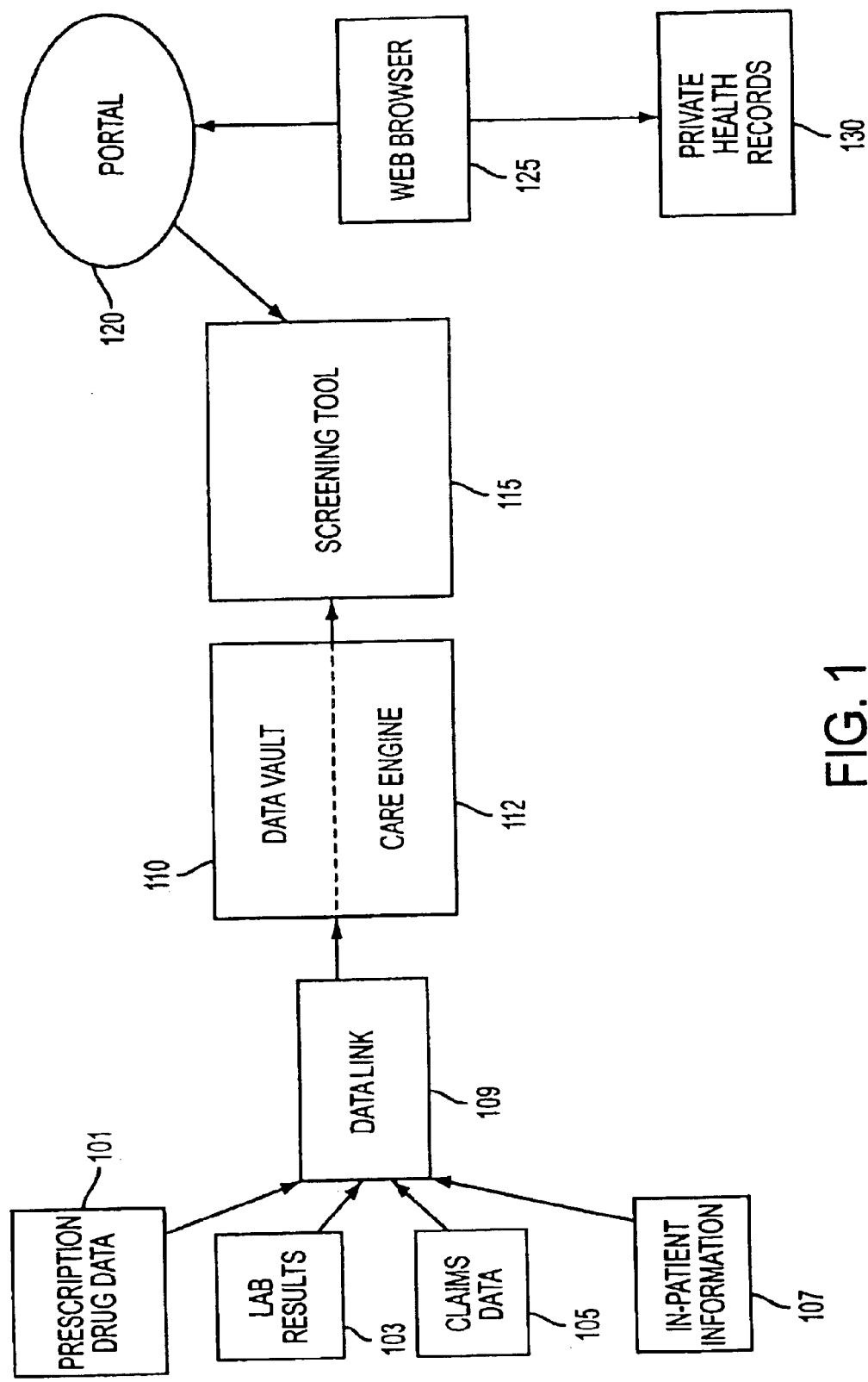
FIG. 1 is a schematic illustration of the system configuration of the present invention.

The present invention as seen in FIG. 1, makes use of state of the art data warehousing capabilities geared toward rapid data transfer, analysis and storage. The DataVault 110 is designed to be highly scalable and capable of being expanded at a low marginal cost. The system offers customers the ability to store patient data securely and provide real-time access to that data. The system eliminates the customer's need to maintain appropriate technology, facilities and personnel for data storage while increasing reporting flexibility. Unlike other healthcare data warehouses that are organized by types of data, such as lab or insurance claims records, the DataVault 110 is designed around individual patients in order to capture all clinical information related to the care provided to the patient. The DataVault 10 also serves as a unifying technological infrastructure component.

The present invention will analyze, collect and report aggregate medical care data, such as prescribing patterns and usage habits. The system can then be used to migrate patients from less effective drugs to more effective drugs or from existing therapies to drugs that are better tolerated. In addition, the system can be used to assist the pharmaceutical industry in identifying untapped markets for new and existing drugs.

Inherent in all of the analysis is access to the system information. Therefore, the system includes the Private Health Record 130, which is a secure, password-protected personal Web page that will be auto-populated by the Care Engine 112 with patient data collected by the DataVault 110. The Private Health Record 130 will also be available to patients within a covered population. Patient's will be able to access their own Private Health Record 130 either through their health plan's Web site or their employer's intranet. The Private Health Record 130 will include the following features: elements of the patient's healthcare history, such as lab, pharmacy and claims data presented in easily understandable format; a patient healthcare diary, which can be used by patients to record the results of self-administered tests, as well as information regarding use of over-the-counter medications and dietary supplements; the ability to "push" relevant health reference information to the patient based on that patient's specific medical data file; the ability to "pull" healthcare information entered by the patient into the Private Health Record 130 into that patient's medical data file; links to the patient's health plan's Web site for eligibility, referral and procedure authorization information; a physician view function which allows the patient to print out a summary of his or her medical information in a physician-oriented format; links to online disease management communities and content; links to health status and health risk assessment tools; and patient-controlled security access to the Private Health Record 130.

Another feature of the present invention allows users or customers to screen patients within a covered population according to clinical criteria defined by the customer using the logic contained in the Care Engine 112. For example, if a customer wants to identify all diabetics within its covered population who are over 50 years old, using a specific drug and have specified laboratory test values which may place those patients at risk, the Company would query the Case Finder as described later, to locate those patients.

Another feature of the present invention is the Risk Stratifier which uses the Care Engine to stratify populations of high-risk patients according to severity-adjusted disease criteria, co-morbidities and the potential impact of disease through the application of evidence-based clinical standards. The Risk Stratifier enables its customers to select appropriate candidates for disease or case management. In contrast to traditional selection methods, the system does not use historical medical costs as stratification criteria, since these costs may not be a reliable indicator of future healthcare utilization.

The system utilizes a customizable, Internet-based patient management software platform that is designed to assist customers and healthcare and providers in managing patient populations and individuals with complex, acute or chronic diseases. Customers use the workflow platform to: build individualized patient assessments using dynamic conditional logic technology that eliminates irrelevant questions and asks additional questions based on the patient's previous responses; develop an individualized care plan based on the patient assessment data; assign tasks to nurses and patients to ensure compliance with care plan goals; and track and report aggregate and individual clinical, financial and productivity outcomes.

Unlike traditional disease management approaches, the system of the present invention through the CareSystem tool enables its customers to address socioeconomic issues and the impact of disease on a patient's life, including living conditions, access to transportation and other issues that may impact compliance with suggested treatment regimens. In addition, CareSystem feature of the present inventor is capable of effectively managing patients with multiple disease states.

The present invention includes an internet-based care management application portfolio of discrete, easily customizable healthcare applications designed to capitalize on the efficiencies of the Internet to add value for the customers. Several of these applications use dynamic conditional logic and artificial intelligence technology and include: an Internet-based application that enables patients to complete an online medical history form prior to a doctor's visit and which provides a concise medical history summary for the physician; an Internet-based interactive health risk assessment questionnaire designed to enable a provider or patient to assess their health status; a set of Internet-based applications that enables patients with chronic diseases to effectively monitor their own disease and allows providers to oversee the patient's health status; a library of Internet-based patient surveys that provider organizations can use to gather information from patients regarding customer satisfaction with the organization or a particular treatment that has been rendered and an Internet-enabled utilization management application that provider organizations can use to quickly and efficiently obtain approval for hospital admissions and expensive medical procedures.

The system also includes an integrated clinical underwriting suite of tools consisting of software applications, the Care Engine 112, the DataVault 110 and consulting services. Clinical underwriting is premised on the idea that understanding the disease process and the potential impact of anticipated treatment patterns is central to predicting future medical costs. Traditional actuarial and underwriting methods are unlikely to explicitly consider these factors as they are based on historical costs modified by demographic or other macro adjustment factors.

The clinical underwriting suite of tools will involve using clinical decision support software, known as MediSave$^{SM}$, to enable customers to predict specific disease-related costs in a covered population based on epidemiological and demographic data. Customers can use MediSave$^{SM}$ projections to assess potential savings derived from different disease management strategies. In addition, the system will apply the clinical data aggregation and analysis capabilities provided by the DataVault 110 and Care Engine 112 to this population-based analysis to refine these projections by identifying the individuals within the covered population who are being medically mismanaged and whose associated medical costs could be affected by timely treatment intervention. The present invention will improve customers' ability to predict future medical costs.

Technology

As previously stated, the present invention is provided through or as an application service provider so that the additional tools or products can be rapidly implemented and upgraded at low cost. Customers are provided with an Internet-based environment where computation intensive functions are supported with high security, performance, availability and scalability. All of the CareSystem division applications will be processed through a standard Internet browser. The CareSystem workflow software platform uses dynamic HTML and XML software protocols and system interfaces to provide high transaction speed and also integrate with legacy health care information systems efficiently.

The DataVault 110 in a preferred embodiment consists of an Oracle database that sits on a Sun Enterprise 4500 server. The system and DataVault 110 have sufficient capacity to store data for approximately 20 million patients, which may be increased. The system maintains a robotic enterprise tape library with off-site storage as a back-up and recovery facilities.

Customer-specific databases are integrated by an analysis layer and a communications layer using, a multi-tier server architecture. Formal policies and procedures as well as technologies are used to protect the integrity of the systems and the confidentiality of the sensitive data they contain. Performance and availability of the system is maintained through a redundant design that allows for continued operation if critical components fail, as well as automated monitoring to detect failures.

In addition, customers can make clinically-based financial predictions to make informed decisions regarding various care intervention alternatives and the efficacy of medical treatment decisions. For example, customers will be able to decide exactly when to proactively manage patients and intervene in the disease cycle to prevent disease deterioration and avoid high medical costs.

The system provides a comprehensive suite of clinical products and services, which combines proprietary technology with the benefits of the Internet to provide a complete clinical care management solution. The systems applications and services include the ability to: identify and predict clinical errors; guide providers to optimal treatment strategies; aggregate and standardize patient clinical information in a single database; and provide tools to manage patient health.

The present invention includes a multi-dimensional analytical software tool developed to address a number of categories of clinical diseases. The Care Engine 112 uses these proprietary evidence-based clinical matrices, to identify potential diagnostic or treatment errors. The Care Engine 112, covers a broad spectrum of commonly observed disease states and co-morbidities to create a comprehensive view of a patient's health and treatment status.

Matrices are a predefined list or grouping of elements across all of the classes of data including lab elements, drug elements, diagnoses elements, and procedure elements. As an example, procedure elements could be an MRI if the patient is diagnosed with a certain type of disease and should be having certain types of MRIs performed as the normal course of clinical care, the matrix would contain all the appropriate MRI procedure elements. Each element of the matrix is defined and these element definitions are continuously evolving and being redefined based upon current medical information and knowledge. As an example, new drugs continually come on the market and are evolving because of new clinical issues which requires new elements to be defined based upon the new drugs and clinical information. The new elements are incorporated into the appropriate matrices fro keeping the matrices medically up to date.

Further, the matrix defines the context in which you want to group these elements, as an example, a patient diagnosed with high cholesterol would have their data processed in a matrix which would contain all the defined elements for certain cholesterol reducing drugs and the corresponding care considerations.

In addition, the present invention may include disease-specific workflows, artificial intelligence technology and additional division portfolio applications. The system may include, a PPO-based monitoring tool which will establish baseline quality and document variations over time, for a managed care population.

The present invention, as previously described, provides a detection system for patient health risk called the Early Warning Trigger Analysis (EWTA) System. The EWTA is an automated mechanism for the early warning detection of patient health risk which pools together information derived from Claims, Prescription Drugs, Laboratory findings, Procedures, Diagnoses and Utilization reports.

The system will use a combination of: actual medical information supplied by HMO's via data import functions, prepared medical databases (National Drug Codes, ICD-9, CPT-4 etc.); and proprietary coding methodologies for the specification of trigger parameters (the matrices). The system will also provide references to periodicals that will support the early warning findings thus providing physicians a complete package of the findings and support materials for current and future patient care.

The goals of the system are many and include the early detection of hazardous drug combinations based on patient information and the detection of unnecessary use of drugs that are prescribed for the wrong diagnoses. The financial benefits are clear and the most overriding benefit is the chance to save lives based on early risk detection and management.

Implementation of the EWTA system requires a combination of data feed, data entry, and computer processing. In a preferred embodiment all the data feeds and manual data entry will be kept in a Microsoft SQL Server database. All import, data entry, and processing screens will refer to this common database.

Data feeds into the EWTA system are composed of industry standard databases and patient data. The industry standard databases may include, but are not limited to the following: National Drug Codes; LOINC Lab Codes; ICD-9 Procedure Codes; and CPT-4 Diagnoses Codes.

Patient data will include: claims data; prescription drug claims; laboratory analysis; and procedures/diagnoses.

In a preferred embodiment, the above data feeds will be imported via the application from supplied flat ASCII files. In the case of Industry standard databases, the format of importable files is usually part of the documentation.

The importing of patient data will be performed during a data import phase of processing. The format of these files must be fully specified. Currently the system receives information from a single supplier; this facilitates the specification of import file formats. Part of the overall deliverable of this system will be the necessary documentation supplied to other Health Management Organizations so that they may prepare patient data files for input.

The data entry into the EWTA system are composed of system wide configuration initialization values, matrix element definitions, and matrix specification.

System wide configuration initialization values are used as a set of configuration tables to pre-initialize part of the EWTA system. These initialized tables will allow the current design to be extended in many cases, without having to implement additional software. For example, the system will initially receive data from a single HMO, but will be designed to allow importing from other HMO's without additional programming, this functionality is provided via a table, which allows the system to specify the list of active HMO's supplying data.

As previously described, this matrix element definition is a grouping of related information (i.e. Drugs) into a single unit for processing the data. The matrix specification is a grouping of matrix elements along with evaluation criteria parameters for processing the data. Establishment of the matrix elements and matrix specifications will be performed through data entry screens that will be part of the EWTA System.

An example of the present invention as part of an Internet Web Based system is described below in conjunction with FIGS. 4 through 21.

The present invention is comprised of various system components including: System Initialization Tables; Database Table Import; Matrix Elements; Matrix Specification; Matchup Module; and various other Profile related components.

In a preferred embodiment the system will contain a database table used to provide basic initialization and system wide processing values which is referred to as the System Initialization Tables. In most cases the values in these tables will not need to be adjusted once the system is installed. There are however some values that may need to be added or changed.

Figure 4:
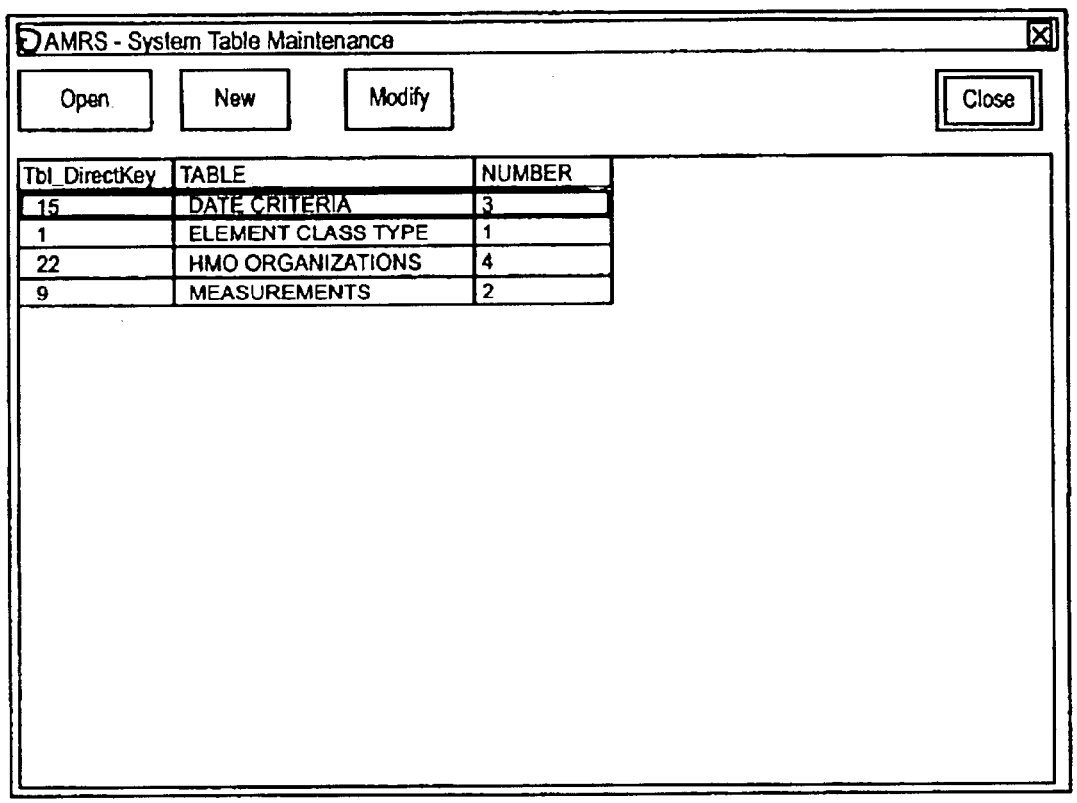
FIG. 4 is an illustrative example of a user interface in a preferred embodiment of the present invention for the Table Maintenance Module.
Figure 5:
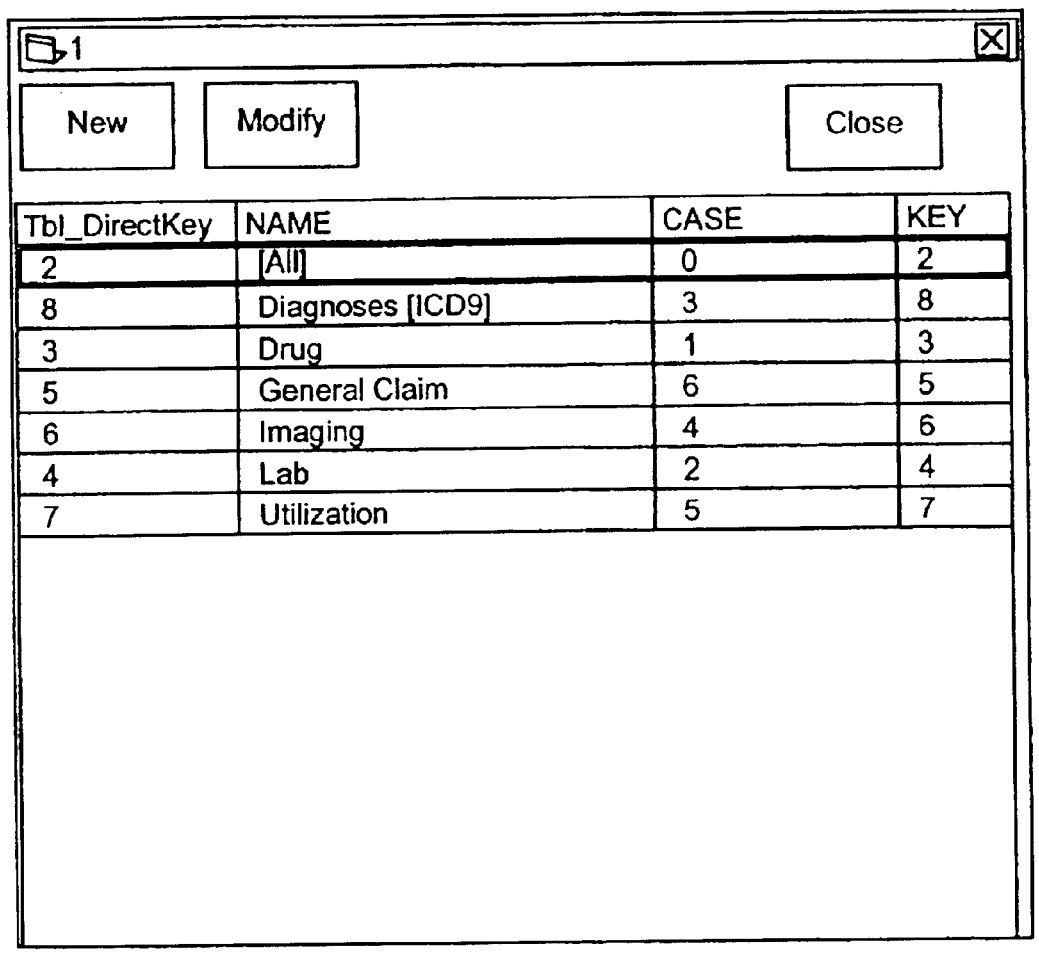
FIG. 5 is an illustrative example of a user interface in a preferred embodiment of the present invention displaying the Table Maintenance Module table selection screen.
Figure 6:
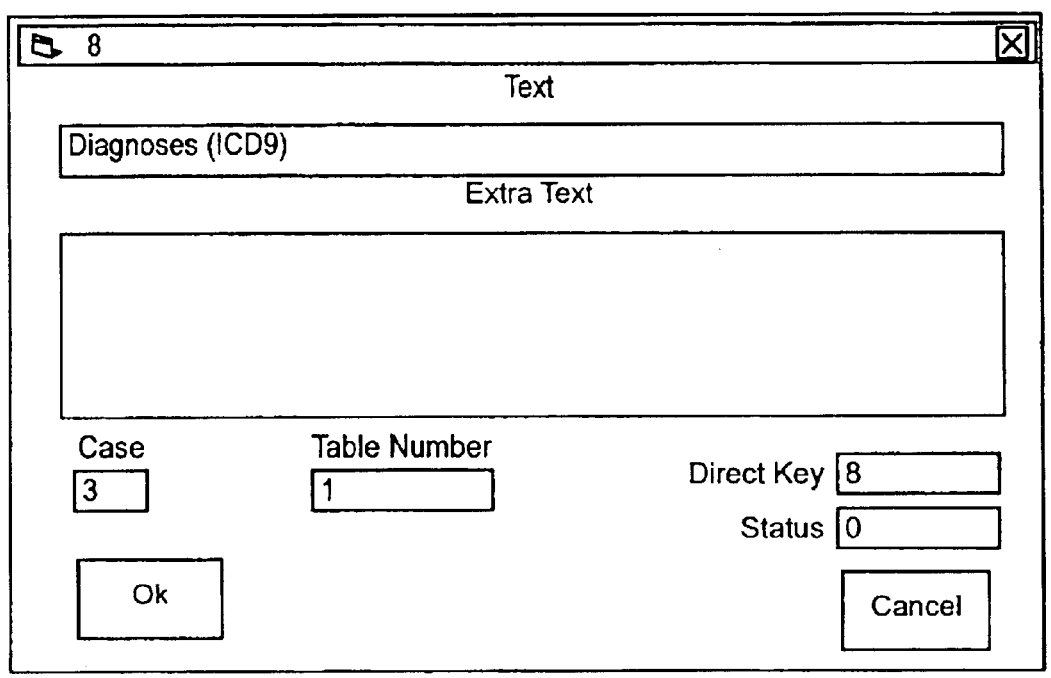
FIG. 6 is an illustrative example of a user interface in a preferred embodiment of the present invention displaying the Table Maintenance Module table modification screen.

The system initialization tables are maintained using the Table Maintenance Module. The Table Maintenance Module user interface screen is depicted in FIG. 4. A table is a list of predefined answers that a user can choose from during data entry, instead of entering free-form data. System tables provide user selections that have specific interpretations. For example, the specification of a time period as "Last 18 Months". The term "Last 18 Months" is understood by the user, as well as by the processing system. The tables themselves are pre-set when the system is installed. New tables cannot be added, and existing ones cannot be deleted. However, you can add, change or delete individual items in a table.

The system tables may include a Date Criteria table that establishes date range parameters such as "Last 12 Months", "Last 18 Months"; a Measurements table that establishes common measurement for criteria entry, such as "High", "Low", "Not Observed"; an Element Class table that establishes a set of element types, such as "Drug", "Lab", which will facilitate the grouping of Elements that are applied to Matrices; and an HMO Organizations table that establishes a set of data suppliers that are maintained in the system SQL Server databases. These table entries provide a simple standard method for user input, as well as well defined values for system interpretation.

Each element of the tables can be opened, created, and modified. The elements contained in a system table can be viewed by selecting the desired table (clicking with the mouse or keyboard navigation keys) and clicking the Open button. The display will change to that shown in FIG. 5.

Further, provided is a sample of the Table Elements that are defined for the Element Class Type system table. New entries in a system table are made by clicking on the New button shown in FIG. 5. Selecting the entry and then clicking the Modify button allows users to make modifications to table entries. In either case, the screen shown in FIG. 6 will be displayed. Most of the system tables will remain unchanged from their initial installation values. However, the system will allow the element and system tables to change.

In addition to the System Initialization Tables, the preferred embodiment of the present invention will include a Database Table Import module which is responsible for gathering both predefined industry standard databases and patient information. The user interface screen 700 for the Database Import Module is displayed in FIG. 7. The Database Import Module will be split into two processing areas, which include pre-defined industry tables known within the system as "Standard Databases" and patient medical information known within the system as "Patient Databases".

The Standard Database Table Import Module is used to facilitate system integration with the pre-defined industry tables which will have been pre-imported to their SQL Server counterparts. The current Standard Database options may include the National Drug Codes (NDC), LOINC database tables, ICD-9 International Classification of Diseases and CPT Physicians Current Procedural Terminology.

The National Drug Codes may include the NDC text file, NDC Drug Classes, and NDC Drug Class Cross Reference. Further, there exists a public domain version of these NDC database tables available on the Internet for download. The system also provides detailed file descriptions and relationships to allow applications to import and process the National Drug Codes in a common manner.

The LOINC database tables may be accessed through a public domain version available on the Internet for download. The system also provides detailed file descriptions and relationships to allow applications to import and process the National Drug Codes in a common manner.

The ICD-9 International Classification of Diseases is contained within a database table containing the ICD-9 codes. This table will be imported into the SQL Server Database as is. Should the ICD-9 be supplied in some other format, or via third party files this import process will need to be modified accordingly to reflect the input file specifications.

The Physicians Current Procedural Terminology (CPT) is contained within a database table containing the CPT codes. This table will be imported into the SQL Server Database as is. Should the CPT be supplied in some other format, or via third party files this import process will need to be modified accordingly to reflect the input file specifications.

Assuming well-defined Standard Database input files for these databases, importing proceeds as follows. For Each database file to import, the user specifies the location of database input file adjacent to the button, as seen in FIG. 7, which begins the importing.

To navigate through the system disk drives programmatically, the Browse . . . button 705 may be clicked. Clicking the Browse . . . button 705 will activate the standard Windows File Open Dialog, which allows all disk drives, connected either physically or via network connections to be browsed to find the required data files.

Data Import begins by pressing any of the Import Command Buttons. During data import, the status area at the bottom of the screen will show a running summary of system activity. There will however need to be a way to refresh these tables periodically. Periodic importing of Standard Database Tables is dependent on how the databases will be provided.

Figure 7:
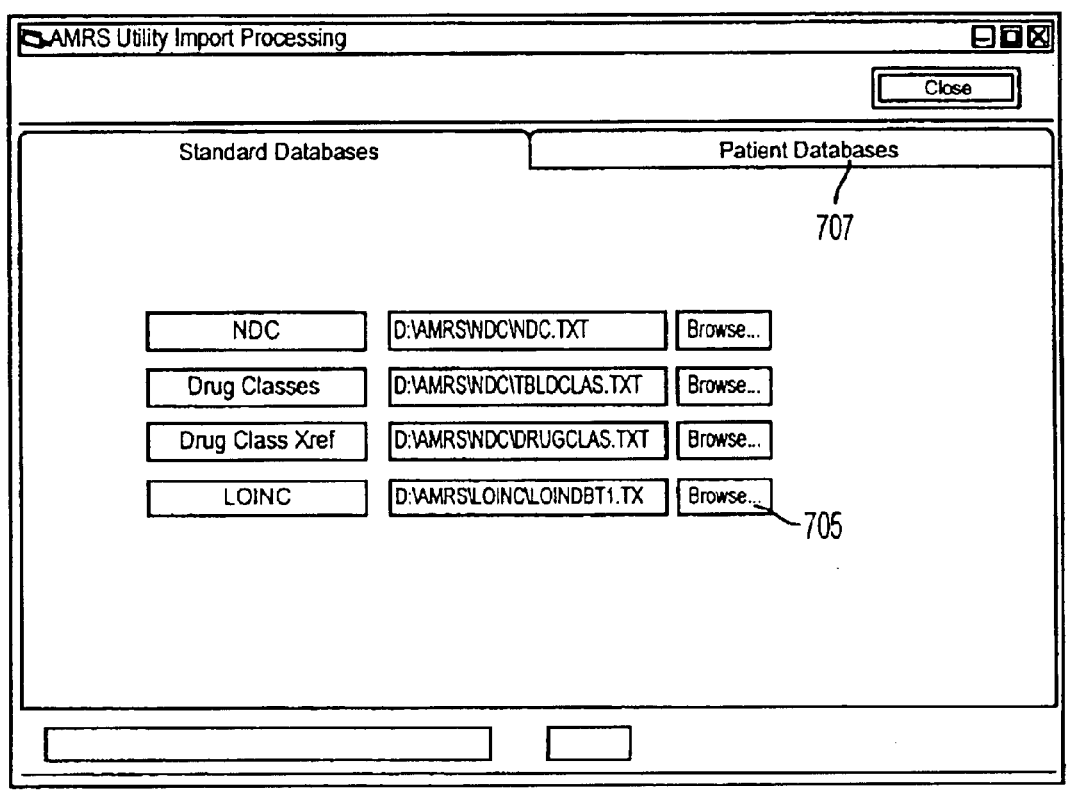
FIG. 7 is an illustrative example of a user interface in a preferred embodiment of the present invention displaying the Database Table Import Module.
Figure 8:
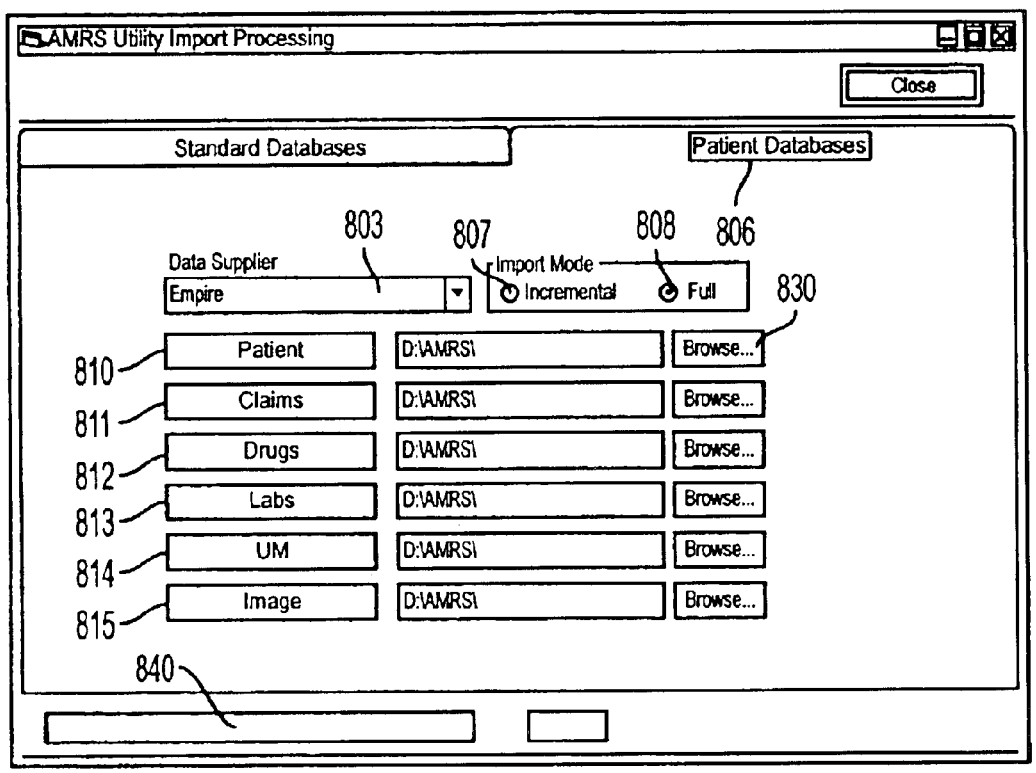
FIG. 8 is an illustrative example of a user interface in a preferred embodiment of the present invention displaying the patient databases.

Patient medical information is imported into the EWTA System by first clicking on the Patient Databases tab 707 in FIG. 7. Selecting the Patient Database tab 707 will display the patient databases user interface screen 800 seen in FIG. 8.

The EWTA System contains several database tables used to store patient information supplied by outside HMO's. It is assumed that all of the patient relevant information necessary for processing will be supplied in some machine-readable form.

The design of this system will provide for on screen viewing of all patient related information in concise on-screen presentations, but may not provide database maintenance capabilities such as Add, Modify, and Delete of patient medical information. Patient information with respect to this system is intended to be a static snapshot.

Patient Medical database import begins with the selection of a Data Supplier from the drop down list 803. The system will be initialized with a single Data Supplier (Empire in this example). If, in the future Patient Medical data is supplied by other sources, the system can define a new data source using the System Table Initialization Module described earlier. Once a new data supplier is established, the supplier will appear in the dropdown list 803. This functionality allows for multiple data suppliers to be maintained in a single SQL Server database, and Matrix processing through the Care Engine can be performed on those single sources.

The Data Supplier will supply the initial patient information. The patient database files will be fully specified, and program logic will be implemented based on the file format specifications. Program logic can be implemented to handle the importing of HMO supplied information on a case by case basis when adherence to the system specification is not possible.

The next step for importing Patient Medical data is to select whether the import source is an incremental upload or a complete import as illustrated in the Import Mode box 806. If the Full radio button 808 is selected, all data for the Data Supplier and import table selected will be deleted from the SQL Server database prior to importing. If the Incremental radio button 807 is selected, the current state of the SQL Server database tables is unchanged, and records supplied via the input tables will be appended to existing database records.

Assuming well defined Patient Medical Database input files the importing proceeds as follows: the user specifies the location of database input file in the fields 820 through 825 located adjacent to buttons 810 through 815 which begins the importing.

To navigate through the system disk drives programmatically, the Browse . . . button 830 may be clicked. Clicking the Browse . . . button 830 will activate the standard Windows File Open Dialog which allows all disk drives, connected either physically or via network connections to be browsed to find the required data files.

Data Import begins by pressing any of the Import Command Buttons 810 through 815. During data import the status area 840 at the bottom of the screen will show a running summary of system activity.

A unique tool of the present invention is the use of matrices for analysis of the imported data. The matrices are defined sets of Matrix Elements. The Matrix Element is the basic unit from which Matrix Criteria are built. The Matrix Element provides a one to many grouping of related information. For example, the grouping of all the National Drug Codes for prescription drugs under a common Element name "Beta Blockers". Whenever the Element "Beta Blockers" is used, the EWTA System will assume this to mean any of the prescription drugs that have been defined to belong to the Element "Beta Blockers." Matrix Elements need to be defined once and then may be used as many times and in as many matrices as are needed by the present invention. For ease of maintenance, Elements are classified as belonging to a specific Element Group Type.

Figure 9:
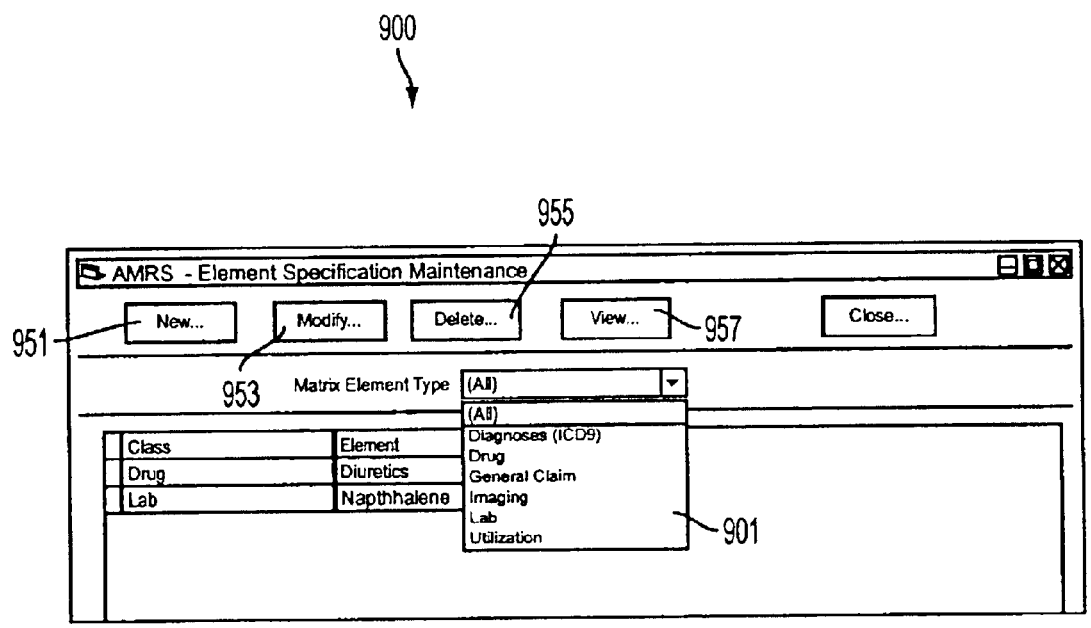
FIG. 9 is an illustrative example of a user interface in a preferred embodiment of the present invention displaying the Matrix Element Maintenance screen.

FIG. 9 shows a user interface screen 900 with a Matrix Element Type drop down list 901 which presents a listing of the Element Types currently being maintained by the system. Upon clicking a drop down selection the Matrix Element Selection list will restrict the presentation of element to those belonging to the selected type. The user may select (All) to view all of the Matrix Elements in alphabetical order.

A Matrix Element is created by clicking the "New" button 951. An existing Matrix Element is modified by first selecting the desired entry to modify by clicking on the item in the list 901 and then clicking the "Modify" button 953. Alternatively the user may begin the modification process by double clicking on the item in the list 901.

New 951 and Modify 953 processing share exactly the same definitional screens with the exception that the initial screen will be presented blank for "New" and with the current or populated data for "Modify". Depending on the Element Type, you will be presented with slightly different mechanisms in which to select the elements that are to be grouped.

Figure 10:
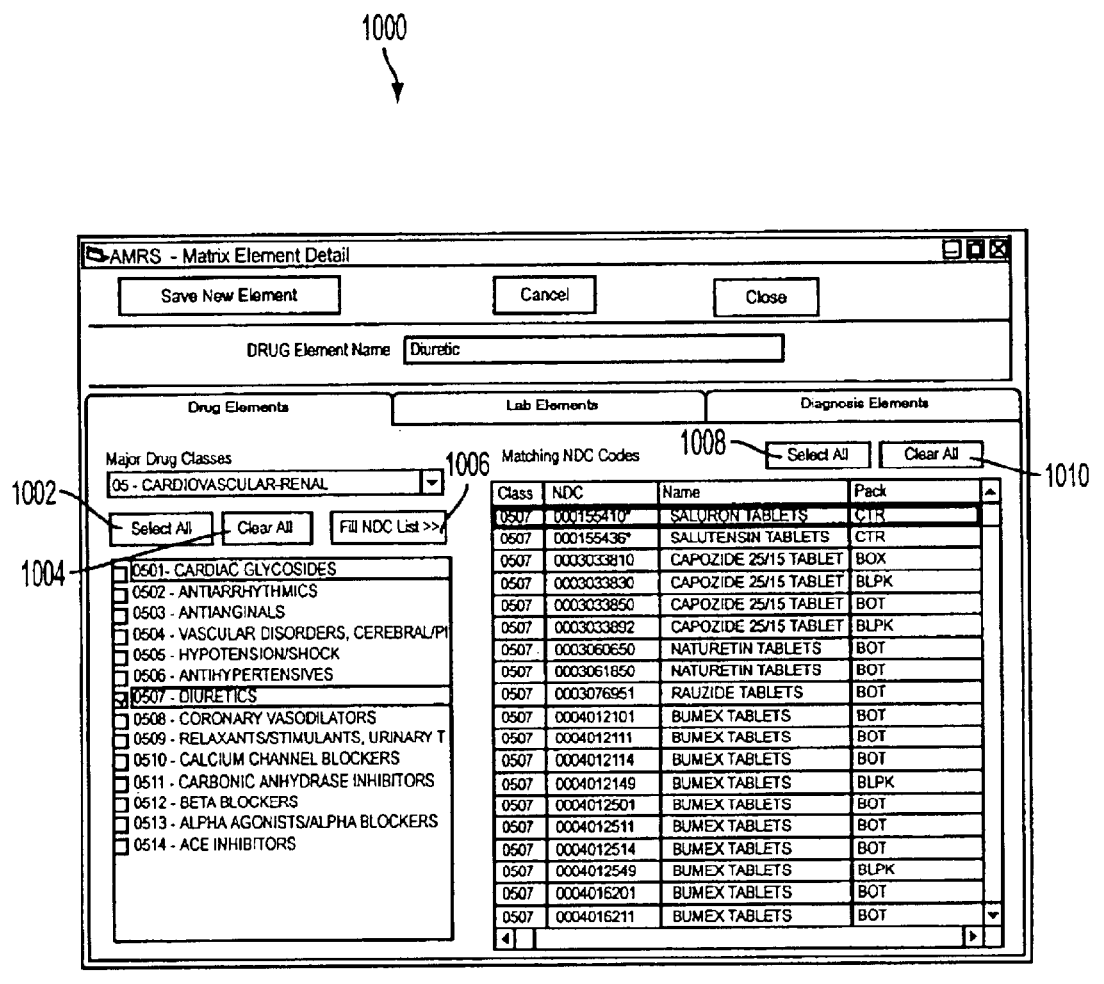

FIG. 10 is a user interface screen 1000 for Matrix Element details for Drug Element and allows the user to break down all the prescription drugs from the National Drug Code database into a set of major Drug Classes. The individual classes that are defined are presented in a drop down list. Processing begins by selecting ("clicking on") a major drug class from the drop down list. Within each Drug Class, the National Drug Code database provides a listing of Sub Classes. Upon selecting a Drug Class, the list of matching Sub Classes will automatically reflecting all of the sub class codes associated with the Drug Class.

Clicking the Select All button 1002 will select all of the Sub Classes currently displayed in the matching Sub Class list box. Clicking the Clear All button 1004 will de-select all of the Sub Classes currently displayed in the matching Sub Class list box. Clicking the Fill NDC List button 1006 will perform a SQL Query and present in the Matching NDC Codes listing all of the Prescription Drugs that match the Drug Class and Sub Class codes that have been selected. Clicking the Select All NDC button 1008 will select all of the Sub Classes currently displayed in the matching NDC Codes list box. Clicking the Clear All NDC button 1010 will de-select all of the Sub Classes currently displayed in the matching NDC Codes list box.

The present invention also has incorporated LOINC data. The LOINC specification database breaks all the LOINC codes down into two classes, Laboratory and Clinical as seen in user interface screen 1100 and field 1101. Based on the radio button selected, the individual classes that are defined for the class are presented in the drop down list. Processing begins by selecting ("clicking on") a LOINC class from the drop down list.

Each LOINC Class is composed of individual Components. Upon selecting a LOINC Class in field 1103, the list of matching Components will appear in the Components list box 1105. Clicking the Select All button 1102 will select all of the Components currently displayed in the matching Components list box. Clicking the Clear All button 1106 will de-select all of the Components currently displayed in the matching Components list box.

Clicking the Fill LOINC List button 1106 will perform a SQL Query and present in the Matching LOINC Codes listing all of the lab tests that match the LOINC Class and components that have been selected. Clicking the Select All LOINC button 1108 will select all of the lab test(s) currently displayed in the matching LOINC codes list box. Clicking the Clear All LOINC 1110 button will de-select all of the lab test(s) currently displayed in the matching LOINC codes list box.

Figure 12:
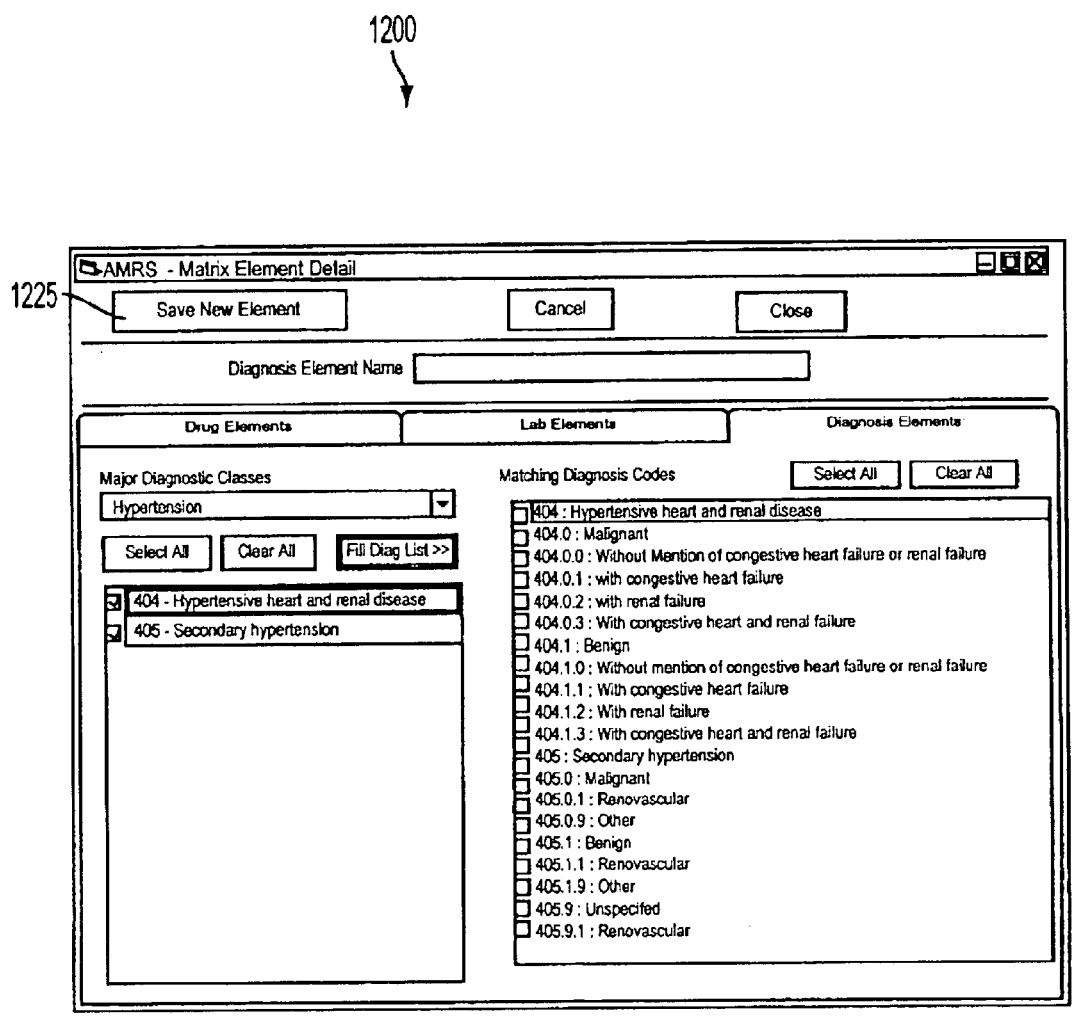
FIG. 12 is an illustrative example of a user interface in a preferred embodiment of the present invention displaying the Matrix Element Maintenance screen with matching Diagnosis codes.

Diagnoses Element definitions follow the mechanism as defined above for Drugs and LOINC and are illustrated in FIG. 12 which depict a user interface screen 1200. Screens similar to the ones outlined for Diagnoses specifications will be implemented for Procedure Elements.

In addition, the system will provide a mechanism to include Elements that fall under the Claim General Category. These elements may include, but not limited to, the following: Number of Admissions; Number of Claims; Number of drugs (any kind); Number of Drugs (specific class); and Number of Drugs (different class). These Elements are derived based on the Patient information and not on standard databases. The specifications of these types of Elements may be part of the system initialization tables.

Depending on whether you are adding a New Element or modifying an existing element, the Save Button 1225 will be captioned accordingly. When you have selected the necessary values that you want to group together to form your Element click the "Save . . . " button 1225.

The Element and its associated values will be saved in the SQL Server database, and will become available for use. A Matrix Element is deleted by clicking the "Delete" button. The Screen will change, presenting the current grouping for the Element to be deleted. The Element will be deleted after the user presses the Confirm Delete Button. Once an Element is deleted, all references made to it with matrices will also be deleted.

The present invention may also include Virtual Elements. A Virtual Element is one in which groupings data values from several classes within the standard database hierarchy are allowed. For example, using the National Drug Codes as an Element can be defined where the actual drugs that are grouped fall into more than one major and sub class, i.e. CARDIO VASCULAR-RENAL and GASTROINTESTINAL, should this be required. The mechanics of building these "Virtual" groupings will be the same with the ability to augment specific values from multiple sources.

Matrix Specification Maintenance

Another important feature of the present invention is the Matrix Specifications which provide the processing modules and the complex criteria that are to be used to detect and report on patients at risk.

Figure 13:
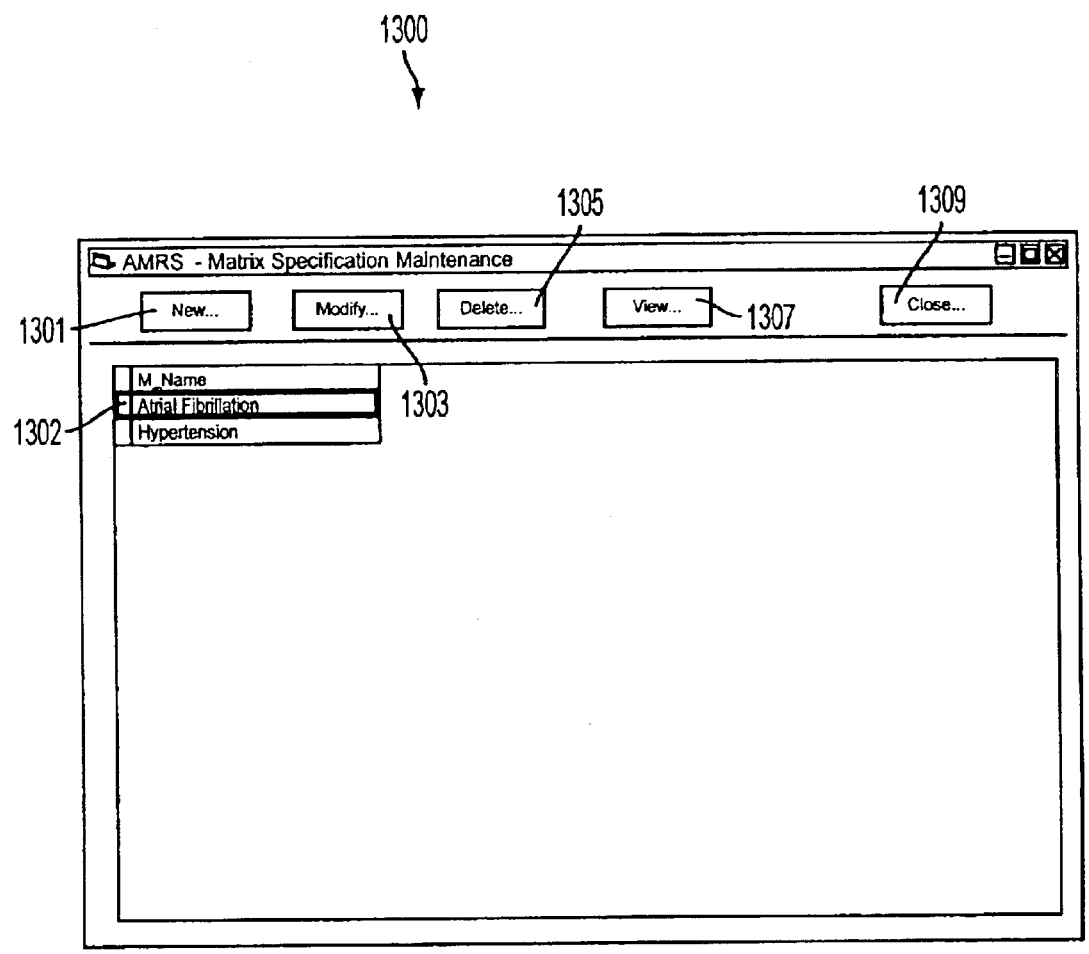
FIG. 13 is an illustrative example of a user interface in a preferred embodiment of the present invention displaying the Matrix Specification Maintenance Module.

The defined Matrix Specifications are presented alphabetically by name as seen in the user interface screen 1300 shown in FIG. 13. A Matrix Specification is created by clicking the "New" button 1301, an existing Matrix Specification is modified by first selecting the desired entry to modify by clicking on the item in the list 1302, then clicking the "Modify" button 1303. Alternatively, the user may begin the modification process by double clicking on the item in the list 1302. New and Modify processing share exactly the same definitional screens with the exception that the initial screen will be presented blank for "New" and with the current or preexisting data for "Modify".

Figure 14:
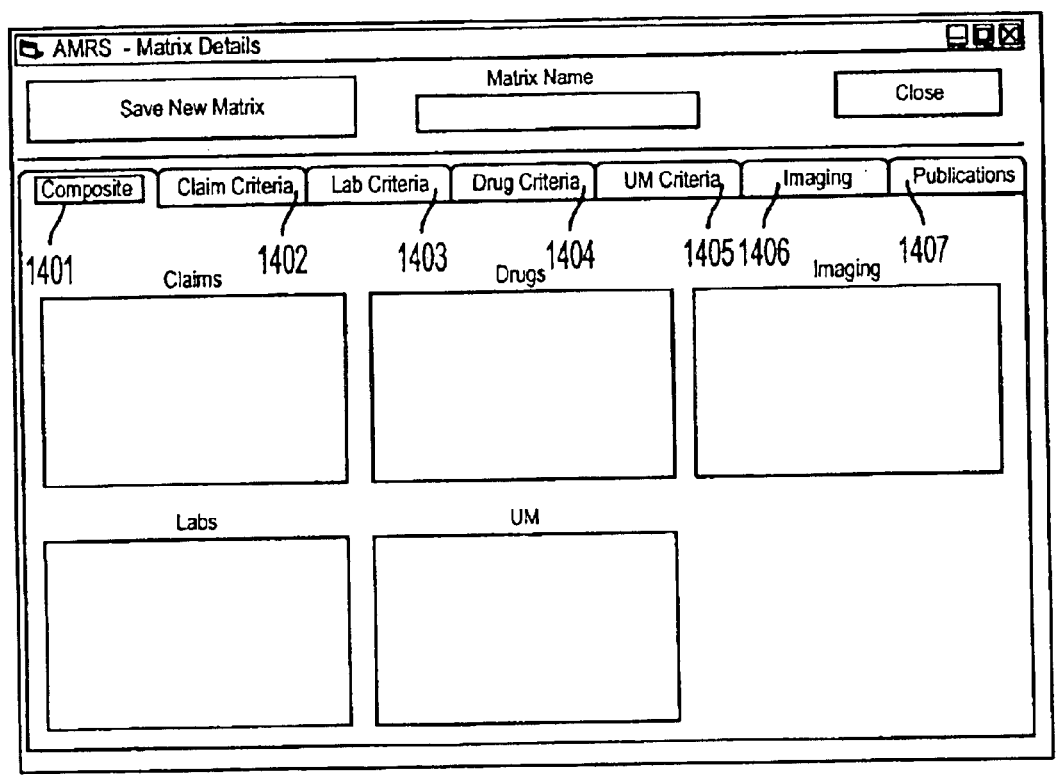
FIG. 14 is an illustrative example of a user interface in a preferred embodiment of the present invention displaying the Composite screen for entry and updating of a Matrix Specification.

To facilitate the entry/updating of Matrix specifications a tabbed dialog box 1400 appears, as seen in FIG. 14, which breaks a matrix definition down into processing components. The composite table 1401 shows on a single display screen 1400 all of the elements in each of the matix columns that are currently defined. The columns may include claims 1402, labs 1403, drugs 1404, UM 1405, imaging 1406, and publications 1407.

Figure 15:
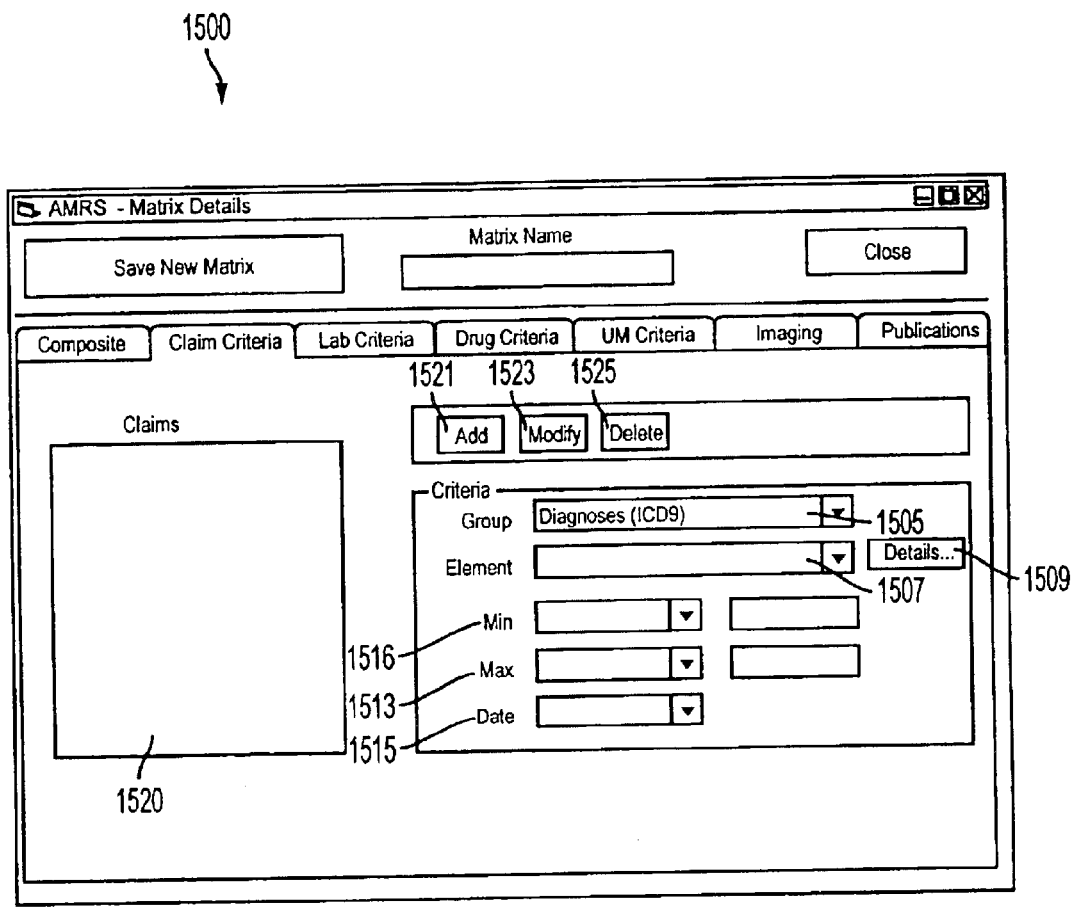
FIG. 15 is an illustrative example of a user interface in a preferred embodiment of the present invention displaying the Claim Criteria screen.

The Claim Criteria tab 1402 is where the Claim column of the matrix is maintained and is depicted in user interface screen 1500 in FIG. 15.

The Claim column of a matrix has access to the more than one grouping of Element Classes. To facilitate the selection of Elements to apply to the Claim Column, the Group drop down list 1505 is used to narrow the Element choices. The Group drop down list 1505 includes the following groups: Diagnoses (ICD9 Elements); Procedures (CPT4 Elements); and General Claim Elements.

Once a selection in the Group drop down list 1505 is made, the Element drop down list 1507 will fill with all the known elements of the selected group. The Element drop down list 1507 is filled with all of the previously defined Elements of the selected group. An Element is selected by clicking on its entry in the Element drop down list 1507. As a convenience, the user may click on the Details button 1509 to present a screen which will show all of the grouped items that are part of the selected Element. As an example, the user may click on the Details button 1509 to view all of the Procedure Codes that are part of a Procedure Element.

To standardize the entry of, and to facilitate the processing of range criteria, The system may employ additional drop down lists, such as a Min 1611, Max 1616, and date 1615 field, which will contain codes to specify a criteria operator as seen in FIG. 16.

The operator will be applied to the adjacent value. Inputting values in both the Min 1611 and the Max 1613 operator value pairs can specify a criteria range. The system can use the "not observed" operator to code Matrix elements that are to trigger when the Element is not found in the data set. For example, the absences of a drug element class. To standardize the entry of, and to facilitate the processing of applicable date criteria, the Date drop down list 1615 will contain codes to specify date criteria.

The creation of a new Matrix Cell for the Claim Criteria Column begins by pressing the Add button 1521. All data entry elements will be reset to initial values.

Selecting the cell in the Claims List Box 1520 and selecting the Modify Button 1523 can modify an existing Matrix Cell in the Claim Criteria Column. Alternatively, double clicking on the item in the Claims List Box 1520 will initiate the Modify operation. All data entry elements will be set from the values contained in the database for the selected cell. An existing Matrix Cell in the Claim Criteria Column can be deleted by selecting the cell in the Claims List Box 1520 and pressing the Delete Button 1525. New or modified values are posted to the SQL Server database by pressing the Save button. The command button panel will return to its original New, Modify, Delete configuration. The selected Matrix Cell, will be removed from the SQL Server database by pressing the Commit Delete. This is your only confirmation that the Matrix Cell is to be deleted. The command button panel will return to its original New, Modify, Delete configuration.

Figure 17:
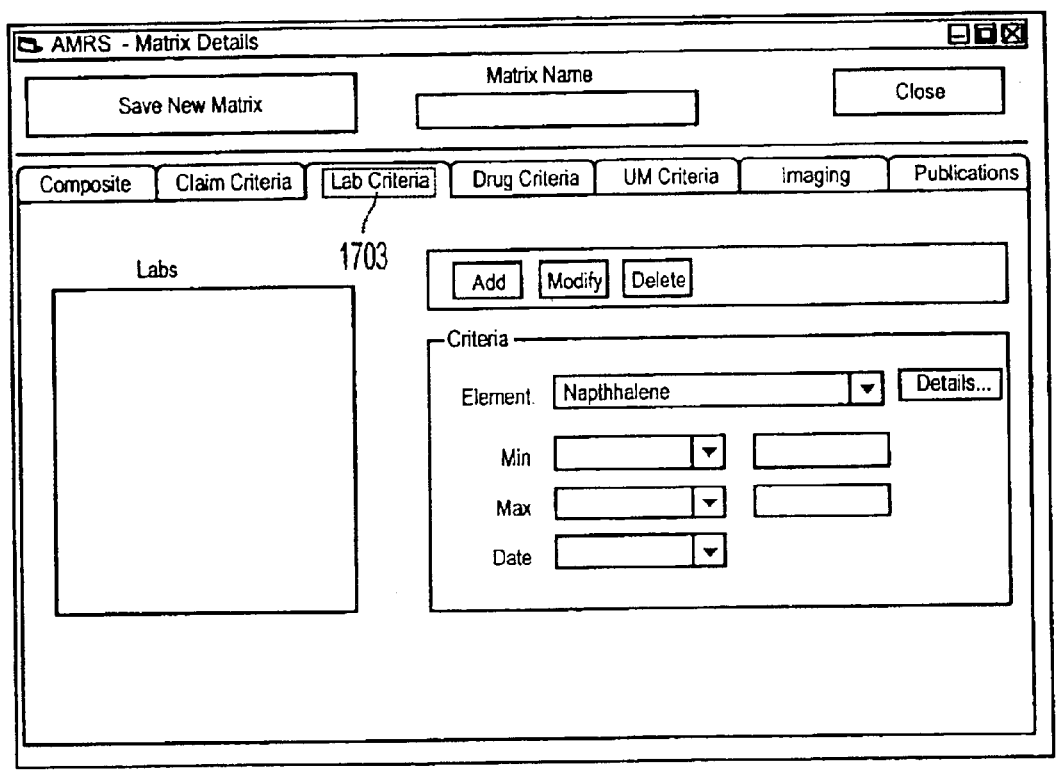
FIG. 17 is an illustrative example of a user interface in a preferred embodiment of the present invention displaying the Lab Criteria screen.

The Lab Criteria tab 1703 is where the Lab column of the matrix is maintained and is depicted in FIG. 17. The mechanics of applying Lab Criteria to the Lab column is exactly the same as those for the Claims column except that only Lab Elements are available in the Element Drop Down list 1707.

Figure 18:
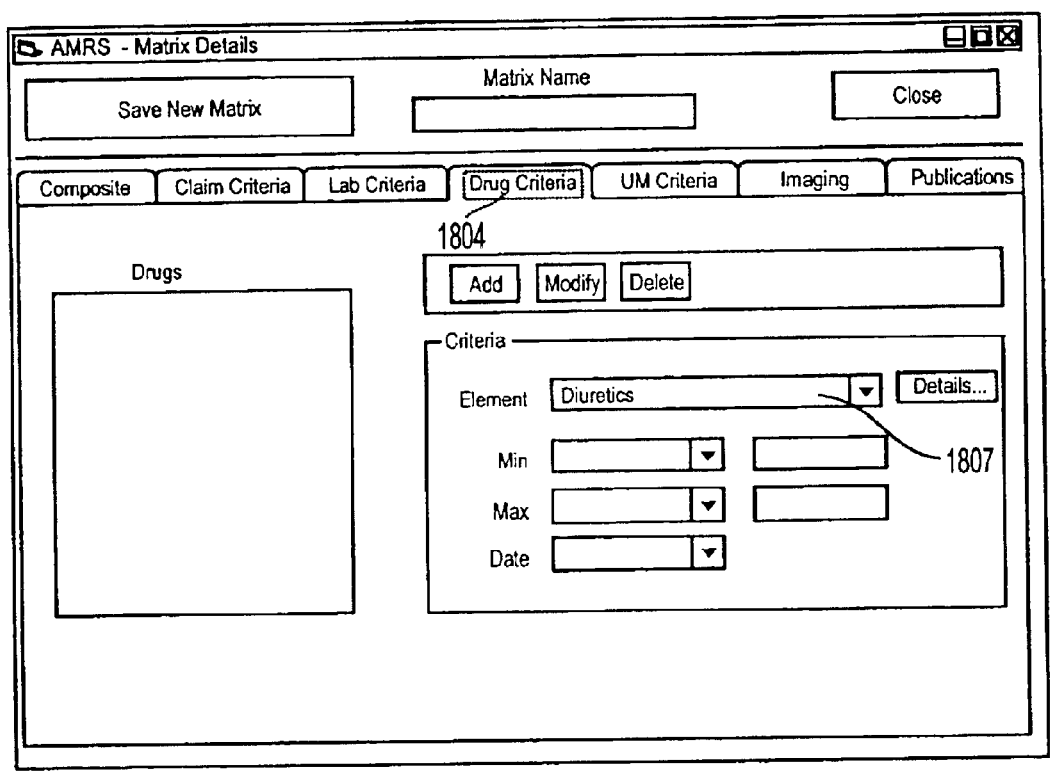
FIG. 18 is an illustrative example of a user interface in a preferred embodiment of the present invention displaying the Drug Criteria screen.

The Drug Criteria tab 1804 is where the Drug column of the matrix is maintained and is depicted in FIG. 18. The mechanics of applying Drug Criteria to the Lab column is exactly the same as those for the Claims column except that only Drug Elements are available in the Element Drop Down list 1807.

Figure 19:
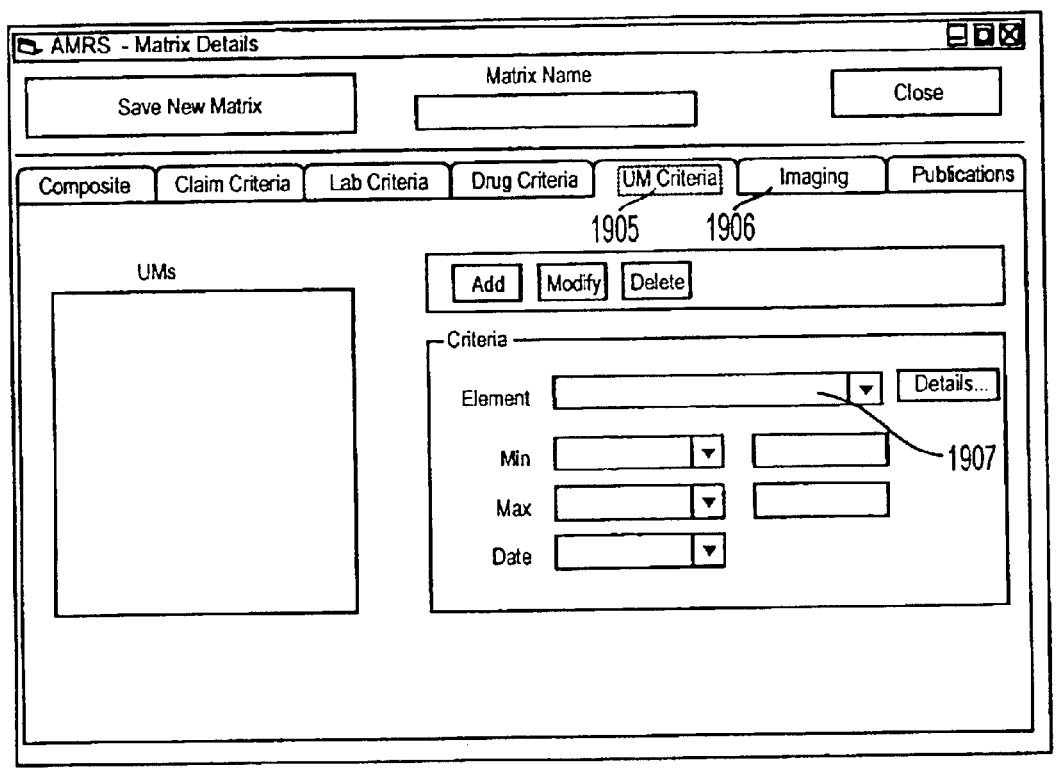
FIG. 19 is an illustrative example of a user interface in a preferred embodiment of the present invention displaying the UM Criteria screen.

The UM Criteria tab 1905 is where the UM column of the matrix is maintained and is depicted in FIG. 19. The mechanics of applying UM Criteria to the UM column is exactly the same as those for the Claims column except that only UM Elements are available in the Element Drop Down list 1907.

The Imaging Criteria tab 1906 is where the Image column of the matrix is maintained. The mechanics of applying Imaging Criteria to the Image column is exactly the same as those for the Claims column except that only Image Elements are available in the Element Drop Down list 1907.

Figure 20:
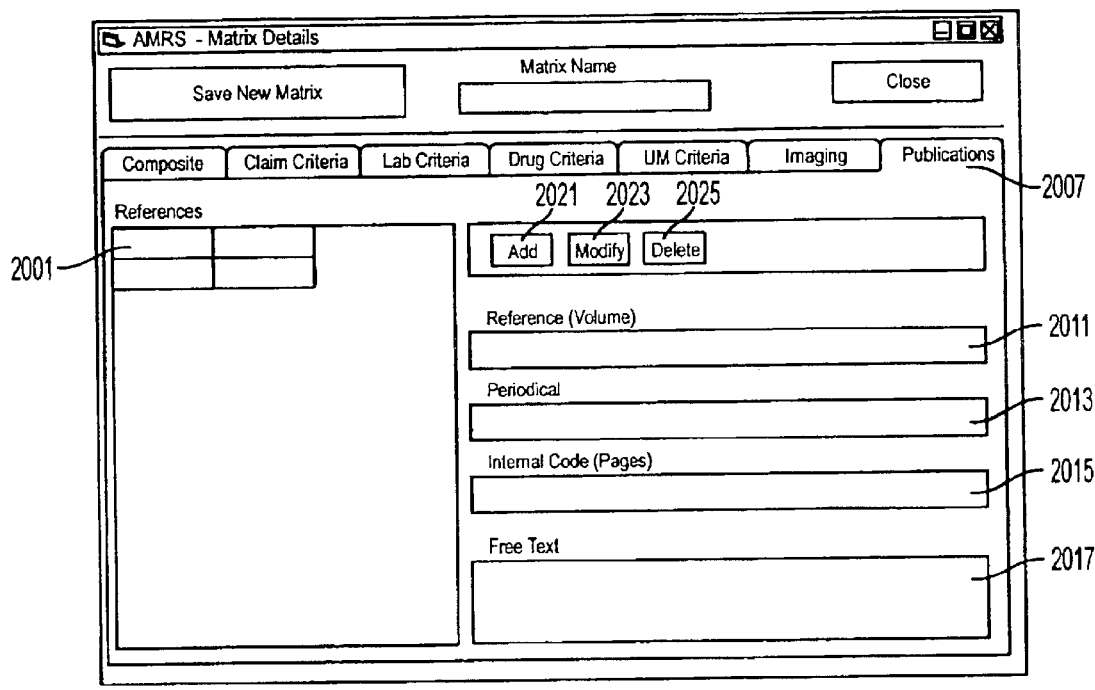
FIG. 20 is an illustrative example of a user interface in a preferred embodiment of the present invention displaying the Publications screen.

The Publications tab 2007 is where the list of periodicals sited for the Matrix is maintained and is depicted in FIG. 20. The Publication screen allows for the input of references, periodicals, internal code and free text. The reference field 2011 is a free edit field describing the reference to a supporting documents. The periodical field 2013 is a free edit field describing the periodical information for a supporting documents. The Code field 2015 is a free edit field describing an internal code or mechanism to retrieve the supporting article from an archive. The Free text field 2017 is a free edit field which allows users to input free text.

The creation of a new reference material by pressing the Add button 2021. All data entry elements will be reset to initial values.

Selecting the reference in the References List Box 2001, and pressing the Modify Button 2023 can modify an existing reference material specification. Alternatively, double clicking on the reference in the References List box 2001 will initiate the Modify operation. All data entry elements will be set from the values contained in the database for the selected reference. An existing reference can be deleted by selecting the reference in the References List Box 2001, and pressing the Delete Button 2025. New or modified values are posted to the SQL Server database by pressing the Save button (not shown). The selected Reference will be removed from the SQL Server database by pressing the Commit Delete button (not shown). This is your only confirmation that the Reference is to be deleted.

Figure 21:
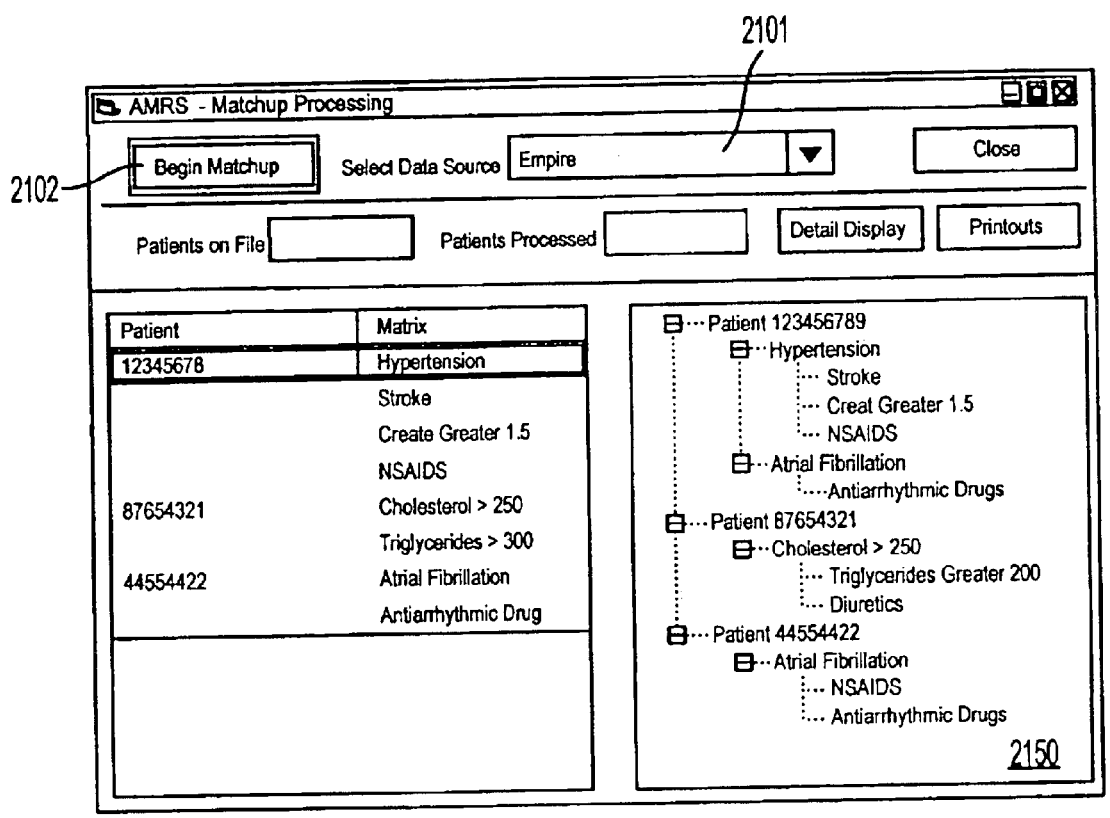
FIG. 21 is an illustrative example of a user interface in a preferred embodiment of the present invention displaying the Matchup Module.

The Matrix Specification Definitions, Element Definitions and Patient medical information are processed in the Matchup Module as seen in FIG. 21. The only user supplied criteria to initiate the Matchup is the selection of the database from the Select Database Drop down List 2101. It is understood that the initial set of Patient Medical data may come from one source, but as the system grows, the system may hold Patient information from several sources simultaneously. The Matchup Module needs to know what patient data set it should be operating on. The processing begins by pressing the Begin Matchup Button 2102. The system will respond with a continuous status display reflecting the current state of processing. The exact information displayed will become clearer as this module is designed and implemented.

At the conclusion of Matchup processing, Patients at Risk listing will be displayed in field 2150. The list will include: Patient Number (by a code which relates all of the claim, drug, labs, urn and imaging tables to a unique patient); Matrix Name (with the name of the matrix specification that was triggered); and Matrix Element (with the matrix cell criteria that caused the warning). This listing may be in the form of a grid, or a hierarchical tree, which will display all the matrix elements that were triggered under each matrix name.

Regardless of the implementation of the Patients at Risk listing, an individual patient in the list will be available for selection with the intent of showing on screen in concise format all of the known medical information contained for the patient in the SQL Server database. It is understood that hard copy printout of the Patients at Risk listing as well as supporting information about the Patient medical information will be included in the design and implementation of the system.

The system, as previously discussed, may receive Patient medical data from one source initially, but this may be expanded. The patient information may consist of several identifiable categories of data. It is imperative that the import files can be linked together using a common linking element. The most obvious linking source would be the Patients Social Security Number, but confidentiality restrictions may not make this possible. In lieu of Social Security Number, the following import table definitions will use a common Link Sequence Number to link the supplied data. The Link Sequence Number is to be maintained by the data suppliers, and will be used by import processing to associate independent data items to a common patient. If data import is considered to be incremental, the data suppliers must ensure that Link Sequence Numbers are uniform with each incremental data set. If on the other hand the data import is a complete load the Link Sequence Numbers must be relevant to the supplied data. There will exist a single Patient Profile record for each Patient supplied. There may be many claim profiles for each Patient profile. There may also be several procedure profile records for each patient and claim profile and several diagnoses profile records for each Patient and Claim profile. In addition, there may be several drug profile records for each Patient profile.

While the preferred embodiment and various alternative embodiments of the invention have been disclosed and described in detail herein, it will be apparent to those skilled in the art that various changes in form and detail may be made therein without departing from the spirit and scope thereof.

We claim as our invention:

1. An early warning detection system for identifying patient health risk, comprising:
    a data base for storing a plurality of medical data and a plurality of patient data, said patient data including medical treatment information for a patient from at least one healthcare provider;
    an analytical care application comprising a set of matrices, wherein each of said matrices contains a plurality of defined elements, wherein said defined elements incorporate said plurality of medical data; and
    a computer processing unit for processing said plurality of patient data through said analytical care application for analysis through said matrices against said plurality of medical data, wherein said computer processing unit automatically makes an alternative treatment suggestion for the patient.

2. The early warning detection system of claim 1, wherein access to said system is available through a web based system.

3. The early warning detection system of claim 1, wherein said medical data is comprised of prescription drug data, lab data, and claims data.

4. The early warning detection system of claim 1, wherein said medical data and said patient data are retrieved over an electronic communications data link.

5. The early warning detection system of claim 1, wherein said analytical care application compares said plurality of patient data for a plurality of patients and identifies patients which may have a health risk due to identified risks defined within an element definition of said defined elements contained within said matrices.

6. The system of claim 1, wherein said plurality of elements are defined based upon clinical criteria.

7. The system of claim 6, wherein said plurality of elements include data related to the severity of disease states.

8. The system of claim 6, wherein said plurality of elements include data related to co-morbidites.

9. The system of claim 1, wherein said plurality of patient data includes a plurality of care data; wherein said plurality of medical data contains a plurality of established standards data; and said analytical care application compares said plurality of care data with said plurality of established standards data.

10. The system of claim 9, wherein said system identifies considerations for improvement of medical care.

11. A method of determining patients with potential health risks, comprising the steps of:
    retrieving a plurality of medical data and a plurality of patient data;
    storing said plurality of medical data and said plurality of patient data in a database, said patient data including medical treatment information for a patient from at least one healthcare provider;
    defining a plurality of elements based upon said plurality of medical data;
    grouping said plurality of elements into a plurality of matrices;
    creating an analytical care application which defines the interaction amongst said plurality of defined elements grouped in said matrices and the interaction of said plurality of matrices;
    processing said plurality of patient data through said analytical care application to indicate instances where some of said plurality of patient data does not correspond with a definition of at least one of said plurality of said elements; and
    automatically making an alternative treatment suggestion for the patient using said analytical care application.

12. The method of claim 11, wherein said medical data is comprised of a plurality of prescription drug data, a plurality of lab data, and a plurality of claims data.

13. The method of claim 11, further comprising the steps of:
    defining said plurality of elements based upon clinical criteria.

14. The method of claim 13, farther comprising the steps of:
    including severity of disease states within said definitions.

15. The method of claim 13, further comprising the steps of:

including co-morbidites within said definitions.

16. The method of claim 11, further comprising the steps of:

comparing patient data related to patient care to medical data related to established standards of clinical excellence; and identifying considerations for improvement of medical care.

17. The method of claim ii, further including the steps of:

providing access to said plurality of patient data, plurality of medical data, and results of said processing said plurality of patient data through said analytical care application over a secure web based system.

18. The method of claim 11, further comprising the steps of:

designing a plurality of clinical care plans based upon said plurality of medical data; and facilitating interaction amongst a plurality of medical personnel for use of said plurality of clinical care plans.

19. The method of claim 18, further including the steps of:

monitoring new patient data for compliance with at least one of said plurality of clinical care plans.

20. An early warning detection system for identifying patient health risk, comprising:

a data base for storing a plurality of medical data and a plurality of patient data, said patient data including medical treatment information for a patient from at least one healthcare provider;

an analytical care application comprising a set of matrices, wherein each of said matrices contains a plurality of defined elements, wherein said defined elements incorporate said plurality of medical data; and a computer processing unit for processing said plurality of patient data through said analytical care application for analysis trough said matrices against said plurality of medical data, wherein said computer processing unit identifies patient health risk by finding potential errors in the treatment of said patient based on available medical history.

21. The system of claim 20, wherein said computer processing unit identifies potential treatment errors automatically.

* * * * *